(12) United States Patent
Gagnon et al.

(10) Patent No.: US 7,305,109 B1
(45) Date of Patent: Dec. 4, 2007

(54) AUTOMATED MICROSCOPIC IMAGE ACQUISITION COMPOSITING, AND DISPLAY

(75) Inventors: MariBeth Gagnon, Rockaway, NJ (US); Roger Taylor, Lilburn, GA (US); James V. Lange, Stone Mountain, GA (US); Tommy Lee, Snellville, GA (US); Carlyn Collins, Atlanta, GA (US); Richard Draut, Snellville, GA (US); Edward Kujawski, Atlanta, GA (US)

(73) Assignee: The Government of the United States of America as represented by the Secretary of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 11/345,863

(22) Filed: Feb. 1, 2006

Related U.S. Application Data

(63) Continuation of application No. 10/001,268, filed on Nov. 13, 2001, now Pat. No. 7,027,628.

(60) Provisional application No. 60/248,948, filed on Nov. 14, 2000.

(51) Int. Cl.
G06K 9/00 (2006.01)
G06K 9/36 (2006.01)

(52) U.S. Cl. ...................... 382/128; 382/233

(58) Field of Classification Search ............... 382/128, 382/233, 305, 232, 240, 248
See application file for complete search history.

(56) References Cited

U.S. PATENT DOCUMENTS

| 4,160,263 A | 7/1979 | Christy et al. |
|---|---|---|
| 4,672,559 A | 6/1987 | Jansson et al. |
| 4,945,476 A | 7/1990 | Bodick et al. |
| 5,139,031 A | 8/1992 | Guirguis |
| 5,216,500 A | 6/1993 | Krummey et al. |
| 5,287,272 A | 2/1994 | Rutenberg et al. |
| 5,544,650 A | 8/1996 | Boon et al. |
| 5,587,833 A | 12/1996 | Kamentsky |

(Continued)

OTHER PUBLICATIONS

Keenlyside et al., "Do Proficiency Test Results Correlate with the Work Performance of Screeners Who Screen Papanicolaou Smears?," *American Journal of Clinical Pathology*, vol. 112, pp. 769-776, Dec. 1999.

(Continued)

*Primary Examiner*—Duy M. Dang
(74) *Attorney, Agent, or Firm*—Klarquist Sparkman, LLP

(57) ABSTRACT

An automated microscope and computer system captures a set of images for a capture area in a plurality of focal planes. The images can then be integrated into composite images for browsing to simulate viewing an item, such as a biological sample, under a microscope. A corrective filter can be constructed from the images to avoid an effect called "tiling." Before capture, variable focal plane error can be avoided by collecting z locations for a set of points in the capture area. During image browsing, entire composite images can be loaded into memory in compressed form. Compressed image portions can be pre-decompressed to avoid delay as a browsing user navigates throughout the composite images. Pre-decompression can be done by a thread separate from the thread performing navigation operations.

15 Claims, 17 Drawing Sheets

U.S. PATENT DOCUMENTS

| | | | |
|---|---|---|---|
| 5,655,029 | A | 8/1997 | Rutenberg et al. |
| 5,677,966 | A | 10/1997 | Doerrer et al. |
| 5,710,842 | A | 1/1998 | Lee |
| 5,768,401 | A | 6/1998 | Csipkes et al. |
| 5,790,308 | A | 8/1998 | Kamentsky |
| 5,793,969 | A | 8/1998 | Kamentsky et al. |
| 5,797,130 | A | 8/1998 | Nelson et al. |
| 5,835,620 | A | 11/1998 | Kaplan et al. |
| 5,889,880 | A | 3/1999 | Doerrer et al. |
| 5,939,278 | A | 8/1999 | Boon et al. |
| 6,031,930 | A | 2/2000 | Bacus et al. |
| 6,034,718 | A | 3/2000 | Hattori |
| 6,101,265 | A | 8/2000 | Bacus et al. |
| 6,226,392 | B1 | 5/2001 | Bacus et al. |
| 6,272,235 | B1 | 8/2001 | Bacus et al. |
| 6,396,941 | B1 | 5/2002 | Bacus et al. |
| 6,404,906 | B2 | 6/2002 | Bacus et al. |
| 6,466,690 | B2 | 10/2002 | Bacus et al. |
| 6,522,774 | B1 | 2/2003 | Bacus et al. |
| 6,606,413 | B1 | 8/2003 | Zeineh |
| 7,027,628 | B1 * | 4/2006 | Gagnon et al. ............. 382/128 |
| 2001/0050999 | A1 | 12/2001 | Bacus et al. |
| 2002/0061127 | A1 | 5/2002 | Bacus et al. |
| 2002/0080481 | A1 | 6/2002 | Tachihara et al. |
| 2002/0118450 | A1 | 8/2002 | Ito et al. |
| 2002/0135678 | A1 | 9/2002 | Bacus et al. |
| 2003/0123717 | A1 | 7/2003 | Bacus et al. |
| 2003/0137494 | A1 | 7/2003 | Tulbert |
| 2003/0170613 | A1 | 9/2003 | Straus |
| 2004/0008894 | A1 | 1/2004 | Zeineh |
| 2004/0027462 | A1 | 2/2004 | Hing |
| 2004/0083085 | A1 | 4/2004 | Zeineh et al. |
| 2004/0256538 | A1 | 12/2004 | Olson et al. |
| 2005/0002547 | A1 | 1/2005 | Torre-Bueno |
| 2005/0002552 | A1 | 1/2005 | Dunn et al. |
| 2005/0084175 | A1 | 4/2005 | Olszak |
| 2005/0110999 | A1 | 5/2005 | Erdogan et al. |

OTHER PUBLICATIONS

Neudorf et al., "Automated Imaging Microscope System," *Linux Journal*, pp. 32, 34, and 35, Feb. 2000.

Vooijs et al., "Computerized Training and Proficiency Testing," *Acta Cytol*, vol. 42, No. 1, pp. 141-147 (abstract only), Jan.-Feb. 1998.

Quarngesser, "The Cytology Proficiency Dilemma: The Case for Computer-Based Testing," *Am Clin Lab*, vol. 15, No. 10, p. 18 (abstract only), Nov.-Dec. 1996.

Greening et al., "The AcCell Series 2000 as a Support System for Training and Evaluation in Educational and Clinical Settings," *Acta Cytol*, vol. 41, No. 1, pp. 153-159 (abstract only), Jan.-Feb. 1997.

Cramer, "Regarding the Validity of Cytology Proficiency Testing," *Diagn Cytopathol*, vol. 22, No. 3, pp. 201-202 (abstract only), Mar. 2000.

Vooijs et al., "CytosafePLUS. A Workstation for Screening, Supervision, Reviewing, Quality Assurance and Education in Cytopathology," *Acta Cytol*, vol. 40, No. 1, pp. 90-96 (abstract only), Jan.-Feb. 1996.

Woodhouse et al., "Proficient or Deficient: On the Razor's Edge: Establishing Validity in Cytology Proficiency Testing," *Diagn Cytopathol*, vol. 20, No. 5, pp. 255-256 (abstract only), May 1999.

"Clinical Laboratory Technologists and Technicians," *Occupational Outlook Handbook*, http://stat.bis.gov/oco/ocos096.htm, pp. 1-4, Jun. 30, 2000.

"Key Phrases in the Handbook," *Occupational Outlook Handbook*, http://stats.bis.gov/oco20016.htm, 1 page, Jun. 21, 2000.

"Vacancies," *Wage and Vacancy Survey of Medical Laboratories*, http://www.ascp.org/bor/mediab/survey/98/, 1 page, Jun. 14, 2000.

"Table 2: Vacancy Rate Percentages for 10 Medical Laboratory Positions," *Wage and Vacancy Survey of Medical Laboratories*, http://www.ascp.org/bor/mediab/survey/98/table2.asp, 1 page, Jun. 14, 2000.

"1998 National Occupational Employment and Wage Estimates: Medical and Clinical Laboratory Technicians," *Occupational Employment Statistics*, http://stats.bis.gov/oes/national/oes32905.htm, 1 page, Jun. 20, 2000.

"1998 National Occupational Employment and Wage Estimates: Medical and Clinical Laboratory Technologists," *Occupational Employment Statistics*, http://stats.bis.gov/oes/national/oes32902.htm, 1 page, Jun. 20, 2000.

"Laboratory Testing for Cervical Cancer: PAP Smear Activities," http://www.phppo.cdc.gov/DLS/clia/cyto.asp, 1 page, Jun. 12, 2000.

"Medical Technologist/Technician," http://www.dir.state.al.us/lmi/CAREER/medtech.htm, 1 page, Jun. 19, 2000.

Goldwasser, "Tripath Imaging Inc.," http://businessbrowser.onesource.com/SharedScripts/Articles/FetchArticle.asp?SearchPhrase=%22pap+smears%22++&RepType=co&Process=TS&article=/TEXT/INVESTEXT/e000508/2103433.htm, pp. 1-4, Mar. 13, 2000.

"Laboratory Corp. of Amer.—Peer Listing Report," 1 page, Jun. 14, 2000.

"CLIA Approved Proficiency Testing Programs—1998," http://www.phppo.cdc.gov/DLS/clia/ptprov.asp, 1 page, Jun. 12, 2000.

"The Medical Laboratories Industry—Pap Smear Test, Federal, Corporate Employee Drug Testing, Aids Testing and Esoteric Test Market," http://www.profound.com/htbin/get_sections, pp. 1-5, Dec. 1999.

"Cytologic Diagnostic Markets in the U.S.," http://www.profound.com/htbin/get_sections, 1 page, Apr. 1997.

"The Medical Laboratories Industry-Summary and Nature, Executive Overview, Status Report, Market Size, Blood Cholesterol, Pap Smear, Federal and AIDS," http://www.profound.com/htbing/get_sections, 1 page, Dec. 1999.

"Diagnostic Market and Technology Trends-Clinical Chemistry, Hematology and Coagulation, Microbiolgy and Virology, DNA Probe Assays, Histology and Cytology, In Vivo Imaging and Conclusion," http://www.profound.com/htbin/get_sections, pp. 1-2, Jul. 1997.

"Bio-Molecular Markers Show Great Promise for Lower Cost In-Office Cervical Cancer Screening," http://www.ampersandmedical.com/News6.html, pp. 1-2, Jan. 18, 2000.

"The AIM 2000 Work System," http://www.ampersandmedical.com/AIM2000.html, 1 page, Jun. 29, 2000.

"The InPath Solution," http://www.ampersandmedical.com/InPath.html, 1 page, Jun. 27, 2000.

"ThinPrep 2000," http://www.cytyc.com/85506Prd/prep2000.htm, 1 page, Jun. 26, 2000.

"Answers to Frequently Asked Questions about the ThinPrep System," http://www.cytyc.com/85506Prd/prepfaq.htm, 1 page, Jun. 26, 2000.

"Summary of Clinical Data," http://www.cytyc.com/85506Prd/prepdata.htm, 1 page, Jun. 26, 2000.

"4pi Analysis, Inc. Corporate Overview," pp. 1-2, Jun. 22, 2000.

"The AcCell Workstation System Features," http://www.accumed.com/cyto/accell.html, pp. 1-2, Jun. 27, 2000.

"Applied Image Group Corporate Overview," pp. 1-5, Jun. 22, 2000.

"Digital Microscopy Image Acquisition," *Biomedical Products Online*, 1 page, Jun. 23, 2000.

"Carl Zeiss, Inc. Corporate Overview," pp. 1-20, Jun. 23, 2000.

"ChromaVision Medical Sys. Corporate Overview," pp. 1-18, Jun. 22, 2000.

"Image Analysis Software," *Biomedical Products Online*, 1 page, Jun. 23, 2000.

"Compix, Inc. Corporate Overview," pp. 1-2, Jun. 23, 2000.

"Diagnostic Instruments, Inc. Corporate Overview," pp. 1-6, Jun. 23, 2000.

"Dicom Imaging Systems Corporate Overview," pp. 1-13, Jun. 22, 2000.

"EasyScan Software 1.0 for Scanning Digital Camera," *Biomedical Products Online*, 1 page, Jun. 23, 2000.
"Electron Microscopy Sciences, Inc. Corporate Overview," pp. 1-3, Jun. 23, 2000.
"General Imaging Corp. Corporate Overview," pp. 1-5, Jun. 22, 2000.
"2D/3D Image Analysis Software," *Biomedical Products Online*, 1 page, Jun. 23, 2000.
"Intelligent Med. Imaging Corporate Overview," pp. 1-3, Jun. 22, 2000.
"International Remote Imag Corporate Overview," pp. 1-15, Jun. 22, 2000.
"Scientific Image Processing Software," *Biomedical Products Online*, 1 page, Jun. 23, 2000.
"Image-Pro Express The Proven Solution," http://www.i-cubeinc.com, pp. 1-3, Jun. 2000.
"Image-Pro Plus The Proven Solution," http://www.ehd.de/ipp.htm, pp. 1-3, Jun. 22, 2000.
"Scope-Pro Plug-In an Image-Pro Solution," http://www.dogpile.com/, pp. 1-3, Jun. 30, 2000.
"Product Information: Software," http://www.i-cubeinc.com/software.htm, pp. 1-2, Jun. 22, 2000.
"Media Cybernetics, L.P. Corporate Overview," pp. 1-6, Jun. 22, 2000.
"MEDX-2000," http://medical.mideosystems.com/medx-2000_features.htm, 1 page, Jun. 22, 2000.
"Medical Applications," http://medical.mideosystems.com/, 1 page, Jun. 22, 2000.
"Nikon, Inc./Instrument Group Corporate Overview," pp. 1-3, Jun. 22, 2000.
"Olympus America Inc./Scientific Equipment Division Corporate Overview," pp. 1-2, Jun. 22, 2000.
"Image Processing Software," *Biomedical Products Online*, 1 page, Jun. 23, 2000.
"Scanalytics, Inc. Corporate Overview," pp. 1-3, Jun. 22, 2000.
"What Women Should Know about Pap Smear Technologies," http://www.cytopathology.org/paptech.htm, 1 page, Jun. 9, 2000.
"The National Breast and Cervical Cancer Early Detection Program," http://www.cdc.gov/cancer/nbccedp/about.htm, pp. 1-6, Jun. 21, 2000.
Collins, "The Challenge of Cytology Proficiency Testing," pp. 1-2, Dec. 4, 1997.
"SpectRx," http://www.spectrx.com/cancer2.html, 1 page, Jun. 15, 2000.
"Table V-1 Cervix Uteri Cancer (Invasion)," *SEER Cancer Statistics Review 1973-1997*, 1 page, Jun. 2000.
"Table V-2 Cervix Uteri Cancer (Invasion)," *SEER Cancer Statistics Review 1973-1997*, 1 page, Jun. 2000.
"Table V-3 Cervix Uteri Cancer (Invasion)," *SEER Cancer Statistics Review 1973-1997*, 1 page, Jun. 2000.
"Table V-4 Cervix Uteri Cancer (Invasion)," *SEER Cancer Statistics Review 1973-1997*, 1 page, Jun. 2000.
"Table V-5 Cervix Uteri Cancer (Invasion)," *SEER Cancer Statistics Review 1973-1997*, 1 page, Jun. 2000.
"Revised Certificate Fees All Labs," http://www.hcfa.gov/medicaid/clia/feesched.htm, 1 page, Jun. 12, 2000.
"Types of CLIA Certificates," http://www.hcfa.gov/medicaid/clia/certypes.htm, 1 page, Jun. 12, 2000.
"List of Approved Accrediting Organizations Under the Clinical Laboratory Improvement Amendments (CLIA)," http://www.hcfa.gov/medicaid/clia/accrdorg.htm, 1 page, Jun. 12, 2000.
"List of Exempt States Under the Clinical Laboratory Improvement Amendments (CLIA)," http://www.hcfa.gov/medicaid/clia/exemstat.htm, 1 page, Jun. 12, 2000.
"1998's Currently Approved Proficiency Testing Programs for CLIA," http://www.hcfa.gov/medicaid/clia/ptlist98.htm, pp. 1-2, Jun. 12, 2000.
"Total CLIA Laboratories Registered Self-Selected Laboratory Types," http://www.hcfa.gov/medicaid/clia/statregi.htm, 1 page, Jun. 12, 2000.
"Percent of CLIA Labs by Certificate Type," http://www.hcfa.gov/medicaid/clia/statcer.htm, 1 page, Jun. 12, 2000.

"CLIA Update Division of Laboratories and Acute Care Services Health Care Financing Administration Jan. 2000," http://www.hcfa.gov/medicaid/clia/statupda.htm, pp. 1-2, Jun. 12, 2000.
"CLIA Final Rules, Amendments to and Clarifications of Regulations and Clinical Laboratory Improvement Advisory Committee (CLIAC) Recommendations," *Advocacy CAP Government and Professional Affairs Resources*, http://www.cap.org/html/advocacy/capdocs/cliachrt.html#11, pp. 1-13, Jun. 21, 2000.
Valente, "Computer-Based Cytology PT," http://www.cytopathology.org/bulletin/Feb98.bulletin/compcyt.html, 1 page Jun. 19, 2000.
"Guidelines for May-Jun. 1997 Proposed Guidelines for Primary Screening Instruments for Gynecologic Cytology," *ACTA Cytologica*, http://www.acta-cytol.com/Admin/97may-guidelines.htm, pp. 1-9, Jun. 19, 2000.
"Table V-6 Cervix Uteri Cancer (Invasion)," *SEER Cancer Statistics Review 1973-1997*, 1 page, Jun. 2000.
"Table V-7 Cervix Uteri Cancer (Invasion)," *SEER Cancer Statistics Review 1973-1997*, 1 page, Jun. 2000.
"Table V-8 Cervix Uteri Cancer (Invasion)," *SEER Cancer Statistics Review 1973-1997*, 1 page, Jun. 2000.
"Table V-9 Cervix Uteri Cancer (Invasion)," *SEER Cancer Statistics Review 1973-1997*, 1 page, Jun. 2000.
"Figure V-1 SEER Incidence and U.S. Mortality Rates Cervix Uteri by Race," *SEER Cancer Statistics Review 1973-1997*, 1 page, Jun. 2000.
"Figure V-2 SEER Incidence and U.S. Mortality Rates Cervix Uteri by Race," *SEER Cancer Statistics Review 1973-1997*, 1 page, Jun. 2000.
Feld et al., "Subpart H—Participation in Proficiency Testing for Laboratory Performing Tests of Moderate or High Complexity, or Both," *Virtual Hospital The Apprentice's Assistant*, http://www.vh.org/Providers/CME/CLIA/LabGuidelines/H855Cytology.html, pp. 1-2, Jun. 14, 2000.
"Regulatory Closure of Cervical Cytology Laboratories: Recommendations for a Public Health Response," *MMWR Recommendations and Reports*, http://www.cdc.gov/epo/mmwr/preview/mmwrhtml/00050479.htm, vol. 46, pp. 1-7, Dec. 19, 1997.
"Department of Health and Human Services, Health Care Financing Administration," *Federal Register*, vol. 65, No. 53, pp. 14510-14512, Mar. 17, 2000.
"Department of Health and Human Services, Health Care Financing Administration," *Federal Register*, vol. 65, No. 53, http://www.phppo.cdc.gov/DLS/clia/docs/fr17mr00.htm, pp. 1-5, Mar. 17, 2000.
"General Program Description," http://www.hcfa.gov/medicaid/clia/progdesc.htm, 1 page, Jun. 12, 2000.
"A Proposed Methodology for Evaluating Secondary Screening (Rescreening) Instruments for Gynecologic Cytology," http://www.cytology-iac.org/other/methodology.htm, pp. 1-3, Jun. 14, 2000.
"U.S. Home Diagnostics and Monitoring Device Markets," *Market Engineering Consulting Report*, Report #5813-54, pp. 1-4, Nov. 1998.
"U.S. Clinical Laboratory Information System Markets: End-User Study," *Customer Engineering: End-User Survey*, Report #5284-48, pp. 1-4, Feb. 1999.
"Cervical Cancer: Independent Studies Confirm Performance of Screening Products," *Cancer Weekly*, 1 page, Apr. 11, 2000.
"FDA Approves Marketing of Alternative to Pap Smear," *Wall Street Journal*, 1 page, Jun. 21, 1999.
"UPDATE: Aetna US Healthcare," *Modern Healthcare*, 1 page, Sep. 13, 1999.
"Monarch HealthCare to Implement New Technology for Detecting Cervical Cancer; Monarch Members Provide Access to More Effective ThinPrep Pap Test," *Business Wire*, pp. 1-2, Jun. 1, 2000.
"Aetna Agrees to Cover New Pap Test," *Boston Globe*, 1 page, Sep. 3, 1999.
"TriPath Announces National Agreement with LabCorp to Offer AutoPap(R) Primary Screening System Multi-Year Arrangement Provides Use of AutoPap," *PR Newswire*, 1 page, Apr. 25, 2000.
"TriPath Announces Conclusion of Share Distribution to Creditors of Neuromedical Systems," *PR Newswire*, 1 page, May 10, 2000.
"Ampersand Medical Enters into Agreement with Cleveland Clinic Foundation to Conduct Clinical Study in China InPath System Holds Promise for Mass Screening of Under-Served Populations," *PR Newswire*, 1 page, Jun. 1, 2000.

"Human Papillomavirus (Cervical Cancer): Company to Offer Latest HPV Test," *Tuberculosis & Communicable Disease Weekly*, 1 page, Feb. 1, 2000.

"Digene Announces Expanded Reimbursement for Hybrid Capture (R) II HPV Test-Covered by Health Plans Representing 125 Million People," *PR Newswire*, 1 page, May 17, 2000.

"Physicians for Women's Health, Nation's Largest Women's Health Group Practice, Adopts Hybrid Capture(R) 2 HPV Test as the Preferred Method for ASCUS Triage," *PR Newswire*, 1 page, Jun. 5, 2000.

"Biotechnology and Medicine: Close Look at Diagnostic Imaging," *Industries in Transition*, 1 page, Dec. 19, 1999.

"Olympus Offers Endoscopic Images," *Japan Industrial Journal*, 1 page, Feb. 5, 1998.

"National Electronic Attachment Inc.'s FastAttach has Direct Interface to Dicom-Imaging's ImagExplorer," *Business Wire*, 1 page, May 15, 2000.

"Dicom's Imaging Software Enabled for Transmission of Electronic Image Attachments," *Business Wire*, 1 page, Mar. 9, 2000.

"Digene's Hybrid Capture(R) II HPV Test Named Biotechnology Product of the Year," *PR Newswire*, 1 page, Apr. 14, 2000.

"Clinical Laboratory Improvement Advisory Committee," http://www.phppo.cdc.gov/dls/cliac/cliac0999.asp, pp. 1-18, Oct. 3, 2000.

Cross, "Fast Fourier Transforms," http://www.intersrv.com/~dcross/fft.html, pp. 1-8, Nov. 6, 2000.

Fourier.pas program listing, Don Cross, http://www.intersrv.com/~dcross/fft.html#pascal, pp. 1-9, Nov. 6, 2000.

"DelphiX2000.07.17," http://www.yks.ne.jp/~hori/DelphiX-e.html, pp. 1-2, Nov. 6, 2000.

"Readme (The Independent JPEG Group's Free JPEG Software)," Independent JPEG Group, pp. 1-13, Nov. 6, 2000.

"System Architecture," Independent JPEG Group, pp. 1-17, Nov. 6, 2000.

"Next Generation Microscopic Imagine Workstation," *BLISS*, http://www.bacuslabs.com/bliss.html, pp. 1-4, Oct. 17, 2000.

Declaration of MariBeth Gagnon, 3 pp. including Exhibits A and B, unavailable pub. date.

Declaration of Edward Kujawski, 1 p., unavailable pub. date.

"AUDF Funds Software Project," Sep./Oct. 1996 ITS Newsletter, 3 pages, http://www.its.unimelb.edu.au/newsletter/1996/September-October/AUDF.html, Oct. 8, 1996.

Afework et al., "Digital Dynamic Telepathology—the Virtual Microscope," In Proceedings of the AMIA '98 Fall Symposium, 5 pages, 1998.

Ferreira et al., "The Virtual Microscope," In Proceeding of the AMIA Annual Fall Symposium, pp. 449-453, Oct. 1997.

\* cited by examiner

AUTOMATED MICROSCOPIC IMAGE ACQUISITION COMPOSITING, AND DISPLAY

CROSS REFERENCE TO RELATED APPLICATIONS

This application is a continuation of U.S. patent application Ser. No. 10/001,268, filed Nov. 13, 2001, now U.S. Pat. No. 7,027,628, issued Apr. 11, 2006, which claims the benefit of U.S. Provisional Patent Application No. 60/248,948, filed Nov. 14, 2000, all of which are hereby incorporated herein by reference.

ACKNOWLEDGMENT OF GOVERNMENT SUPPORT

This invention was made at the Centers for Disease Control and Prevention. Therefore, the United States Government has certain rights in this invention.

FIELD

The field relates to methods and systems for acquiring, compositing, and displaying microscopic images, such as images captured from a camera observing an item under a microscope.

BACKGROUND

Skilled medical professionals can detect a variety of disease-related conditions by observing biological specimens with a microscope. For example, in a Pap smear examination, a trained observer can detect abnormalities in cells taken from a test subject's cervix. Such abnormalities are associated with cervical cancer or pre-malignant conditions, such as cervical dysplasia. Early detection and treatment of such conditions have greatly reduced deaths from cervical cancer.

To perform a Pap test, a biological specimen obtained from cervical cells is prepared and placed on a glass slide. Then, the slide is observed under a microscope by a trained technician or a team of technicians. For example, a cytotechnician might pre-screen a slide by identifying various regions of interest for consideration by a pathologist, who makes the final determination as to whether the sample indicates significant abnormalities. The cytotechnician and the pathologist rely upon their training and experience to determine how to screen a slide. Such professionals must demonstrate their proficiency at properly screening slides before they are qualified to perform screening for actual test subjects.

Training professionals to perform these and other cytological examinations typically involves extensive education, including observation and discussion of training slides. The training slides demonstrate a variety of challenging scenarios, such as those possibly encountered during actual screening. The accurate identification and grading of histological specimens from a variety of tissues (such as gastrointestinal, breast, and neurological tissue) requires experience with a large number of such slides.

Acquiring such a set of training slides is a challenging undertaking. First, the slides should demonstrate biological samples that present various conditions explained during training. Finding such exemplary biological samples may be difficult because certain conditions may be rare. Further, the slides are subject to repeated observation and handling and thus tend to deteriorate over time. Finally, a particular slide may be in great demand but be unavailable because it is being used by another student.

Thus, there is a need for a better way to provide a microscopic view of a biological sample for a variety of purposes, such as for training and certifying medical professionals.

SUMMARY OF THE DISCLOSURE

In one embodiment disclosed herein, a plurality of images are captured during observation of an item by an automated system. A computer system sends directives to an automated microscope to move the stage to various locations within a capture area. The microscope can also move to plural focal planes for the capture area. The captured images are then integrated into composite images. For example, during integration, adjacent images in the same focal plane can be joined together and stored to a computer-readable medium, such as a hard disk. The item can be any number of objects, such as a biological sample.

The composite images can then be browsed by a computer system running browsing software. The browsing software thus simulates viewing the biological sample under a microscope. In some embodiments, composite images for additional magnifications can be generated from the original composite images to simulate viewing with different microscope objectives.

In certain embodiments, a corrective filter can be generated by processing characteristics such as brightness and color values from the captured images. The corrective filter can then be applied to the captured images to avoid an effect called "tiling" that can result when images are joined.

Before image capture, software can collect proper z location settings for a set of locations within the capture area to indicate a uniform z location with respect to the item being viewed. Subsequently, error due to variations in the focal plane can be avoided during image capture by consulting the z location settings and interpolating a proper z location setting for the location being captured. The z location settings can be acquired for one focal plane and applied to other focal planes.

During browsing of the composite images, a set of complete composite images for the focal planes can be loaded into memory in compressed form. To avoid delay when browsing the image, portions of the composite image likely to be next viewed can be decompressed before being viewed. A priority scheme determines which of the images are to be pre-decompressed.

Other techniques for avoiding delay while viewing images include transferring decompressed images directly to video memory and maintaining a cache of decompressed images in video memory.

The foregoing and other features and advantages of the invention will become more apparent from the following detailed description of disclosed embodiments which proceeds with respect to the accompanying drawings.

DETAILED DESCRIPTION OF SEVERAL EXAMPLES

The present invention includes methods and apparatus for capturing images during automated observation of a biological specimen under a microscope, integrating the captured images into composite images, and browsing the composite images.

Automated System

Figure 1:
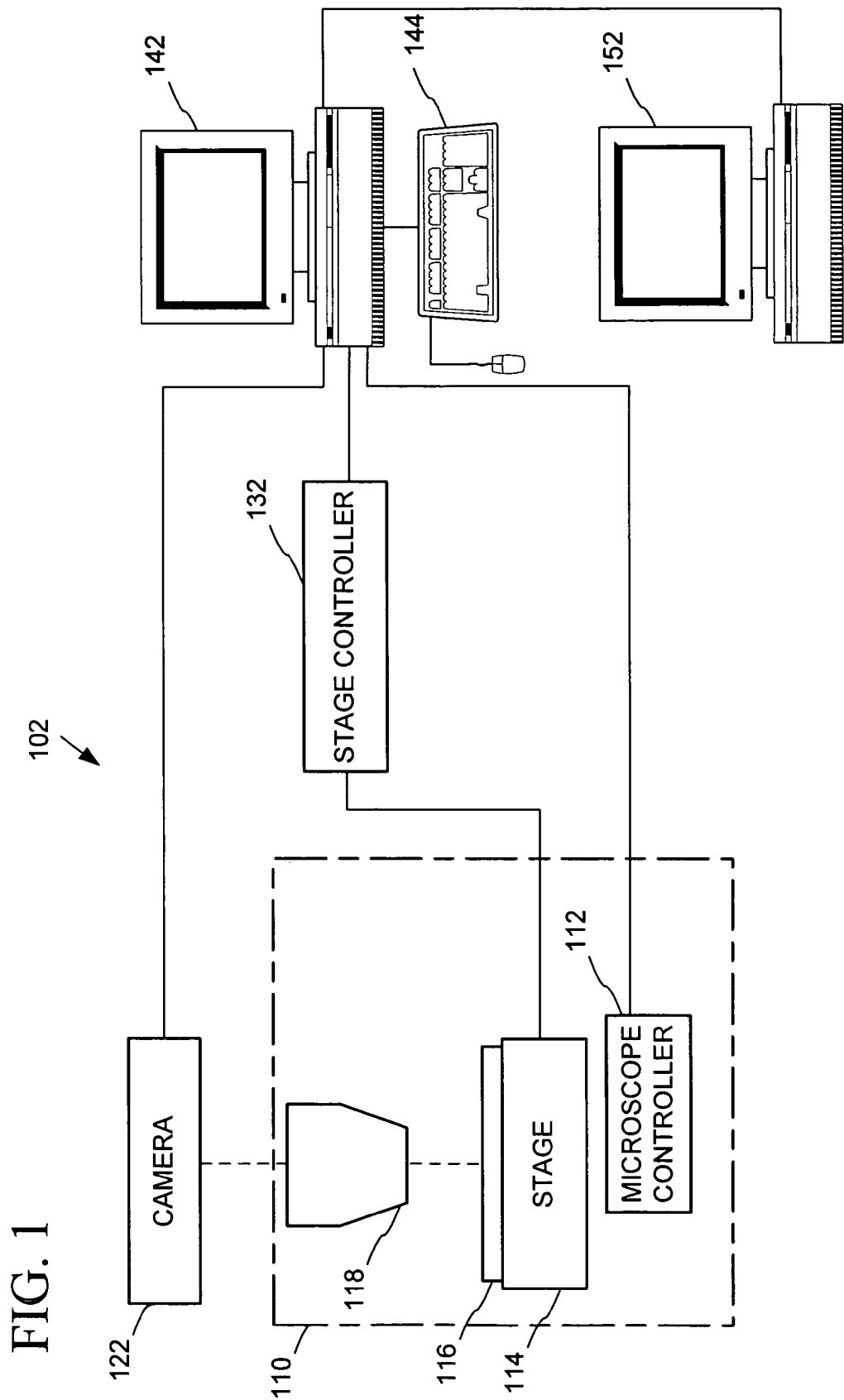
FIG. 1 is a block diagram of a system suitable for carrying out certain features of the invention.

FIG. 1 illustrates a system 102 suitable for carrying out various features of the invention. In the example shown in FIG. 1, a microscope system 110 is controlled by a computer system 142. The microscope 118 is automated in that it can receive and implement directives from the computer system 142 via a microscope controller 112.

For example, the Zeiss Axioscope microscope manufactured by Carl Zeiss, Inc. of Germany can be used in a configuration including 10× and 40× Apochromatic objectives and a LUDL MAC-2002 controller 132 for controlling a LUDL 99S009 motorized stage 114 (manufactured by Ludl Electronics Products of Hawthorne, N.Y.) capable of moving along x-, y-, and z- (i.e., vertical) axes. The motorized stage 114 can be controlled by computer directives from the computer system 142 to the stage controller 132. Although the controller 132 is depicted as outside the microscope system 110, in some arrangements it may be considered part of the microscope system 110. In some arrangements, the same piece of hardware can serve as a microscope controller 112 and stage controller 132. Similarly, other elements shown can be separated or combined to achieve similar results.

The microscope system 110 is typically used to view items on a slide 116, such as a biological sample (e.g., a tissue section or cytological preparation) that has been prepared for viewing via any of a variety of techniques, such as staining. For example, in a scenario involving a Pap test, a sample of cells are taken from the test subject's cervix, prepared for mounting on the slide 116, and viewed using the microscope system 110. A description of a typical process, including a stain used during preparation, is described in Guirguis, U.S. Pat. No. 5,139,031, "Method and device for cytology and microbiological testing," filed Apr. 8, 1991, which is hereby incorporated herein by reference. Liquid-based or conventional preparation techniques can be used.

The system 102 also includes at least one camera 122. The camera 122 is capable of high resolution, close-up photography, such as the SONY DXC-760MD video camera (available from Meyer Instruments, Inc. of Houston, Tex.) with controller and microscope mounting adapter.

The computer system 142 can be used to control the microscope system 110 and capture images from the camera 122. Typically, communication between the computer and various components of the system is achieved via an RS-232 interface convention. In the example, the computer system 142 includes a COMPAQ PENTIUM 160 CPU (available from Compaq Computer Corporation of Houston, Tex.) running the MICROSOFT WINDOWS operating system (available from Microsoft Corporation of Redmond, Wash.), a MATROX MAGIC EISA video capture board (manufactured by Matrox Graphics, Inc. of Quebec, Canada), a keyboard 144, and a high resolution NEC MULTISYNC XP17 21 inch display monitor (manufactured by NEC Corporation of Tokyo, Japan).

The computer system 142 includes computer-readable media, such as main memory (e.g., RAM) and a hard disk, to provide storage of data, data structures, computer-executable instructions, and the like. Other types of media which are readable by a computer, such as removable magnetic disks, CDs, magnetic cassettes, flash memory cards, digital video disks, and the like, may also be used.

In the example, images are captured by a first computer system 142 and then sent to a second computer system 152 for further processing (e.g., compositing). The second computer system 152 is a DELL XEON PENTIUM II computer (available from Dell Computer Corporation of Round Rock, Tex.) running the RED HAT LINUX operating system (available from Red Hat, Inc. of Research Triangle Park, N.C.). The second computer system 152 is set up as a server with high storage capacity (e.g., 136 Gb or more of hard disk space).

Figure 2A:
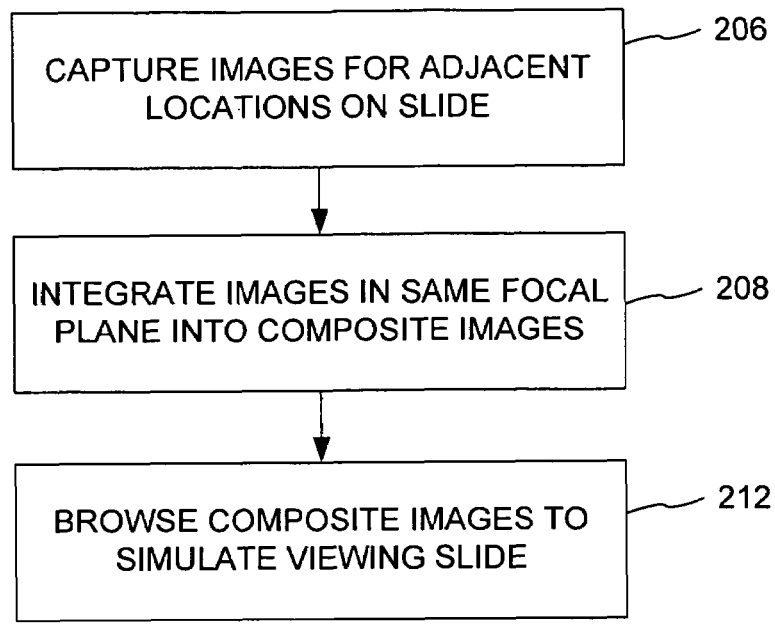
FIG. 2A is a flowchart showing an overview of methods for capturing images, integrating the captured images into composite images, and browsing the composite images to simulate viewing a slide.

Overview of Methods for Capturing Images, Generating Composite Images, and Browsing Composite Images FIG. 2A is a flowchart showing an overview of exemplary methods for capturing images, generating composite images, and browsing the composite images.

In the example, at 206, a set of images for adjacent locations on a slide are captured (e.g., via the camera 122). For example, the set of images may include adjacent locations in a single focal plane, or adjacent locations in contiguous focal planes. Then, at 208, captured images in the same focal plane are integrated into composite images. For example, a set of images can be processed so that an alignment of the images relative to each other is determined. Or, the images can be assigned locations within an area so that the area is composed of a set of more than one image. The composite images can be saved to a computer-readable medium (e.g., a hard disk) so that they can be retrieved at a later time.

Subsequently, the composite images are browsed at 212 to simulate viewing the slide. Browsing typically involves loading the composite images from a computer-readable medium and presenting a view of an image on a computer monitor.

Figure 2B:
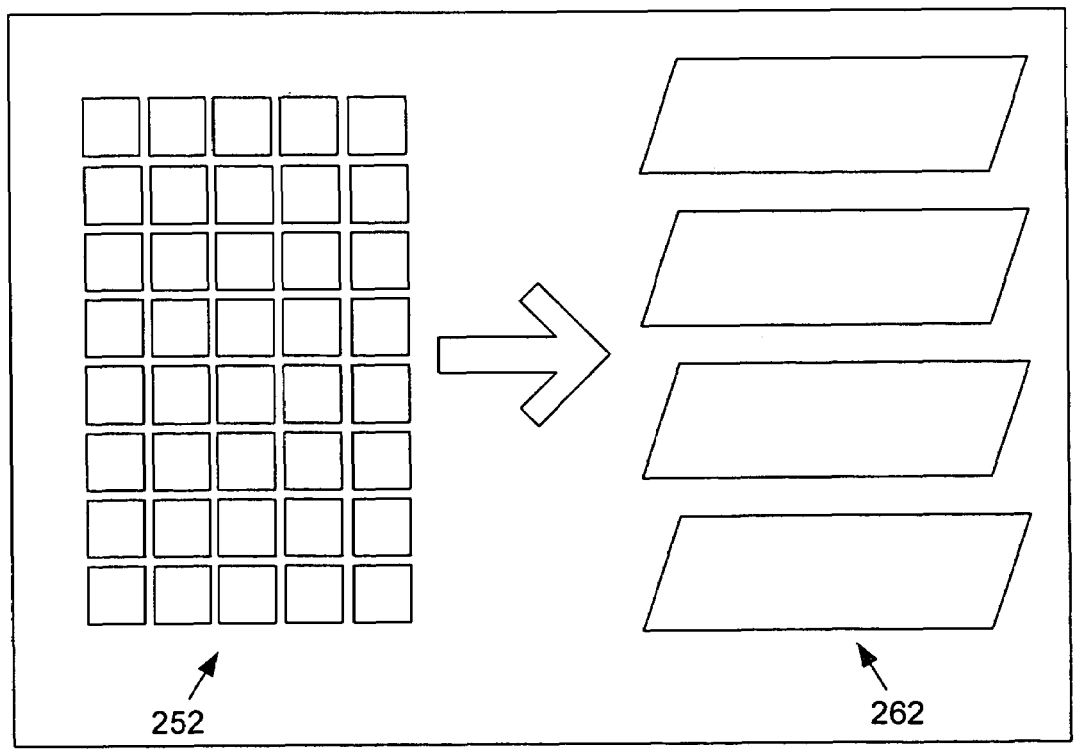
FIG. 2B is a diagram showing an overview of how captured images are integrated into composite images.

FIG. 2B is a diagram showing an overview of how captured images can be integrated into composite images. In the example, a set of captured images 252 are integrated into composite images 262 representing the capture area at four different focal planes. Typically, there is some overlap for the captured images 252 taken from the same focal plane. The overlap can be cropped as the images are integrated. Since integration is similar to sewing together the patches of a quilt, the process is sometimes called "stitching the images together."

Capturing Images Via the Microscope

Figure 3:
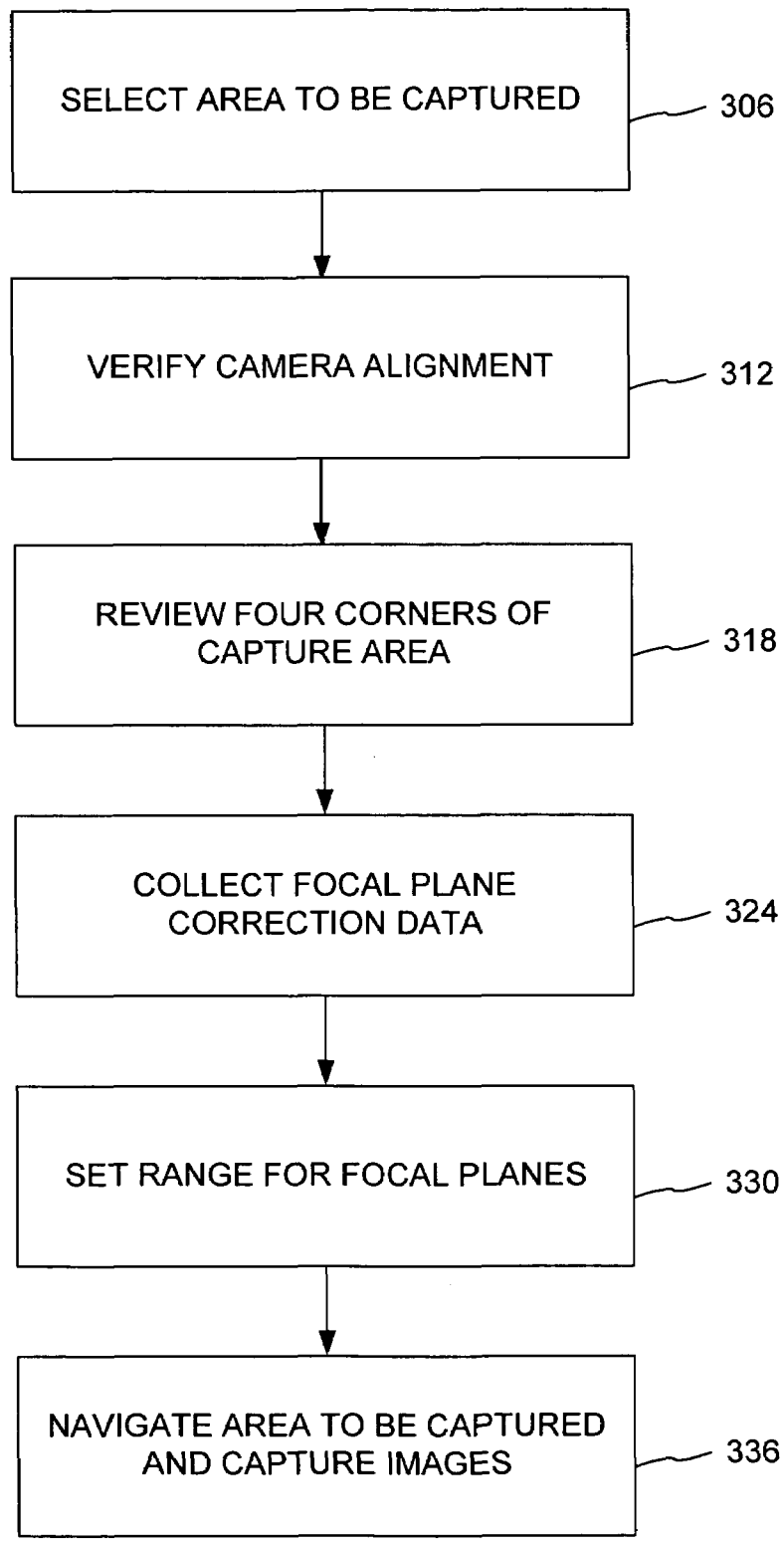
FIG. 3 is a flowchart showing a method for capturing images via an automated microscope.

FIG. 3 is a flowchart showing a method for capturing images via an automated microscope system, such as that shown in FIG. 1. The order of the actions need not occur in the order shown. Typically, the images are captured while observing a glass slide having biological material mounted thereon.

At 306, the area to be captured is selected. Such selection is typically performed by a trained professional who uses experience to determine which areas of the slide serve a particular purpose. For example, if the slide is being captured for purposes of training, an area illustrating a particularly challenging identification scenario might be selected. Since a slide may contain a large amount of biological material, it is sometimes helpful for the microscope operator to generate a printout representing the slide to assist in locating the area to be captured.

For example, the operator can use the automated system 102 or a camera directly on its own (e.g., camera 122) to photograph a glass slide. Typically, a steadying device, such as a copystand, is used, and the photograph is taken at the camera's highest resolution setting. The image can then be downloaded into a computer with image processing software (e.g., ADOBE PHOTOSHOP software from Adobe Systems, Inc. of San Jose, Calif.) and printed out (e.g., as a 1 inch by 3 inch image). The process may have to be repeated until the photograph is determined to be adequate for locating the capture area.

The slide is typically cleaned on both sides before image capture to remove markings, fingerprints, and dust. In the example, the photograph is then used to locate a 5 millimeter by 10 millimeter area of the slide to be captured. The slide is then marked at the lower left corner of the area (e.g., with a fine-point pen that writes on glass). The mark can be used as a reference point. The slide is then loaded onto the microscope with its label to the left side.

Camera alignment is verified at 312. In sum, the camera is aligned with respect to stage movement. For example, the slide can be viewed with any of a variety of programs that provide a view from the camera 122. For example, a utility shipped with the MATROX MAGIC EISA video capture board performs such a function. The microscope 118 is typically set to low power (e.g., a 10× objective) and the stage controls are manipulated (e.g., via a joystick) to align a cell on the top edge of the presented view.

Figure 4:
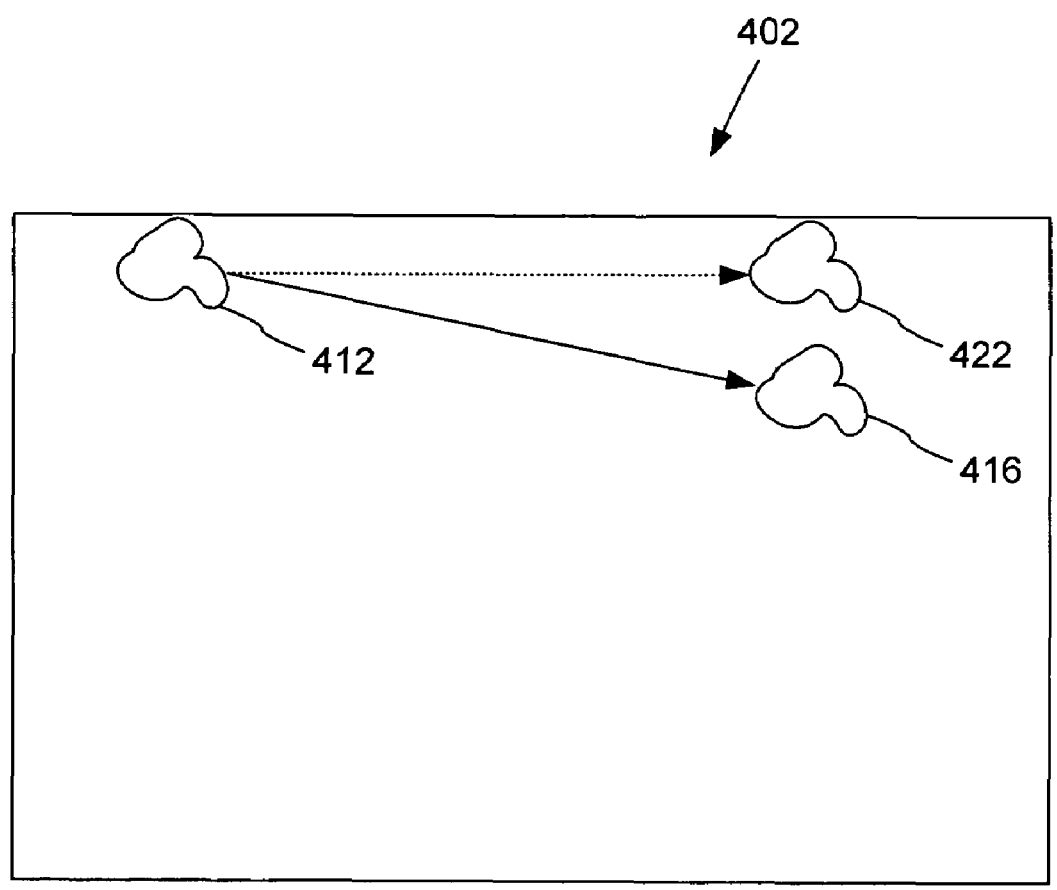
FIG. 4 is a diagram showing how a camera is aligned with respect to microscope stage movement.

FIG. 4 shows such an arrangement. A cell 412 is shown in a view 402 of a slide. The stage controls are manipulated to move the stage from left to right along the x-axis. If the cell 412 does not move parallel to the edge to position 422 (e.g., the cell moves to a location 416), the camera is not properly aligned. The camera is then rotated in either a clockwise or counter clockwise direction and the above technique repeated. When the camera is properly aligned, the cell will move to a location parallel with the top edge (e.g., to the location 422).

A higher magnification (e.g., 40×) can be selected, and light intensity for the microscope set to the highest level. The camera can be adjusted to set its gain to zero and the shutter set to a wide open setting.

At 318, the four corners of the capture area are reviewed. Typically, a first corner (e.g., the lower left corner marked as indicated above) is set, and the other four corners are automatically determined. The microscope operator may wish to verify that the four corners are what were expected. Such a review can take place by viewing the output of the camera 112, instead of viewing the slide through the microscope's eyepiece.

Figure 5A:
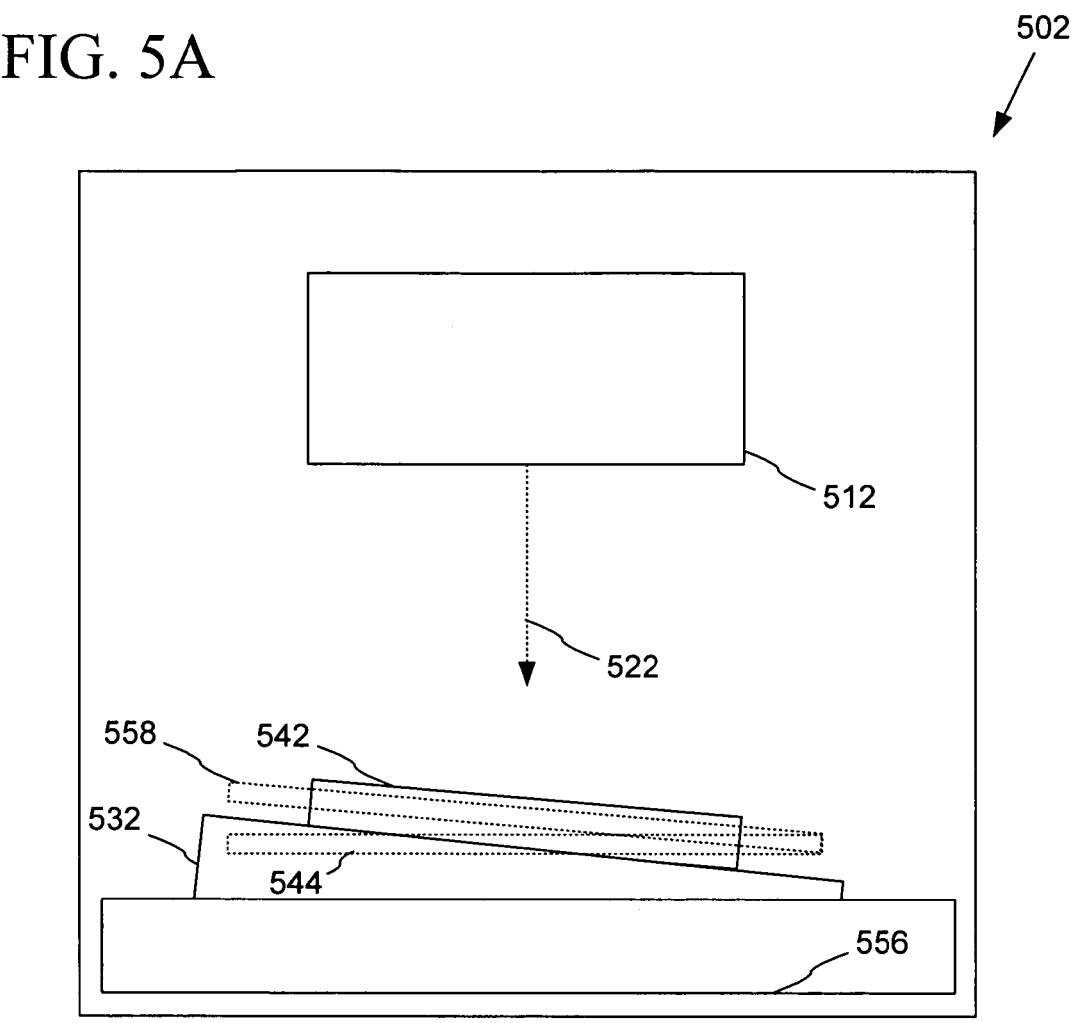
FIG. 5A is a block diagram demonstrating a source of focal plane error.

At 324, focal plane correction data is collected by software. As shown in FIG. 5A, error can result due to imperfections in a microscope system 502. In the example, a microscope 512 is viewing an item 542 on a slide 532 on a stage 556. The drawing is not meant to be to scale, and imperfections of the slide 532 are exaggerated for purposes of illustration.

The edges of an ideal slide would be perfectly and consistently perpendicular to the optical path 522. However, such is not the case in actual slides, due to aberrations in the slide structure (e.g., warping, slant, or bulges), characteristics of the item being viewed, or various imperfections in the system 502. Thus, different portions of the item mounted on the slide surface might be different distances from the stage 556. As a result, when the stage 556 is moved, the item 542 does not maintain a constant distance from the objective of the microscope 512.

The microscope 512 typically views a portion of the item within a particular depth of field 544 at a specified z location (e.g., a particular height above the stage or distance from the objective). However, as the stage 556 is moved, the depth of field 544 might not be at a consistent depth within the item 542. For example, at one point, the z location might correspond to the center of a cell in a biological sample, but when the stage 556 is moved, the z location might well correspond to a location within the slide 554. Or, perhaps the depth of field 544 might fall above the item 542. This problem can result in image capture of useless areas and is sometimes called "variable focal plane error." Although movement is made in an x, y direction, some z correction is needed to keep the microscope's depth of field 544 within the item being viewed.

Figure 5B:
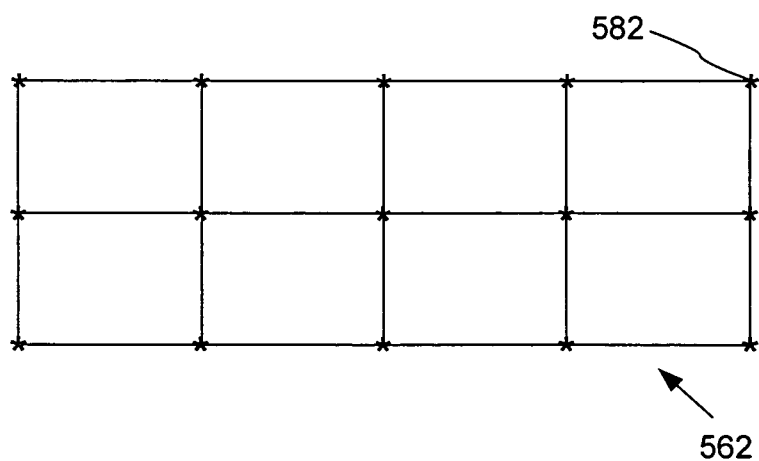
FIG. 5B shows a set of points at which a focal plane can be sampled within an area to be captured to avoid focal plane error.

To avoid variable focal plane error, focal plane correction data can be collected as shown in FIG. 5B. Throughout the area 562 to be captured, the proper z-location of the microscope is determined for a variety of points. In the example, proper z-location is determined by fifteen focal points (e.g., focal point 582) arranged in three equally spaced rows of five equally spaced columns. The rows are at the top, center, and bottom of the capture area 562. Typically, software controlling the microscope automatically navigates to the various locations (e.g., the fifteen locations shown in the example), and the microscope operator manually adjusts the microscope z location to a proper location.

For example, the operator might consistently adjust the microscope z location to a location falling within the region 558 (FIG. 5A), which might correspond to the center or surface of an item (e.g., a cell or set of cells). In this way, the operator indicates a uniform z location with respect to the item at each location. Subsequently, during automated capture, the z position can be adjusted to compensate for the imperfections within the system 502 to effectively capture regions having a uniform z location with respect to the item (e.g., region 558 or similarly oriented regions above or below the region 558).

As the microscope operator indicates to the software that the z locations for each of the fifteen data points are correct, the software stores the proper z location settings. Subsequently, the z depth can be checked at random points throughout the capture area by activating a software feature.

At 330, the focal plane range is set. Typically, the microscope operator first indicates how many focal planes are to be captured (e.g., 5). The operator then navigates to a middle focal plane (e.g., by setting the z-plane settings of the microscope) and indicates to the software that the present focal plane is to be the middle focal plane (e.g., by navigating to the middle and four corners of the plane). Then, a top and bottom focal plane are indicated similarly, and the software automatically interpolates any intermediate focal planes. The focal plane can be set to cover the top, middle, and bottom of an item or a region of interest within an item. For example, when examining a biological specimen, the focal plane range can be set to cover the top, middle, and bottom of a cell, or other structure.

Once the area to be captured has been selected and the various adjustments made to the microscope, the operator directs the software to commence image capture, and the software navigates the area to be captured and captures images at 336. During navigation throughout the area, the focal plane correction data is used to adjust the z location of the microscope system to avoid variable focal plane error. Although correction data may be collected for only one focal plane (e.g., the center focal plane), the data can be propagated for use in other focal planes (e.g., all five focal planes).

Figure 6:
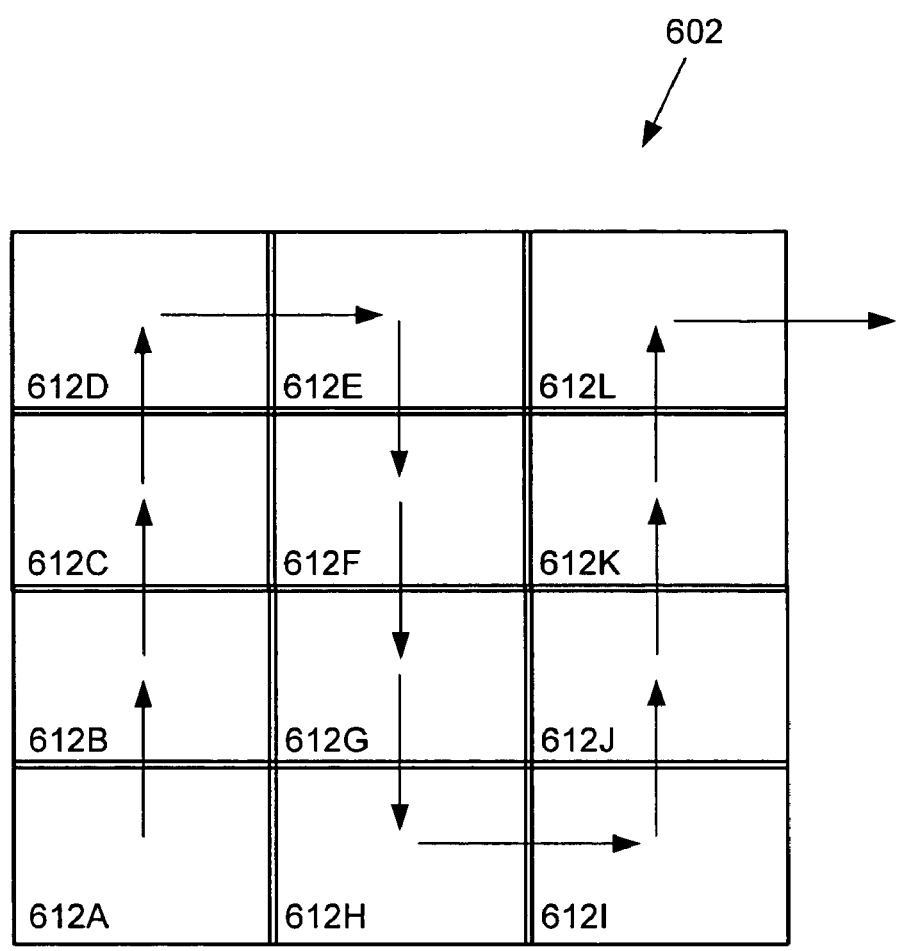
FIG. 6 is a block diagram showing a typical image capture arrangement.

Typically, capture of the image proceeds as shown in FIG. 6. Capture begins at one corner (e.g., upper right or lower left) of the capture area 602, and then proceeds from one area to the next. For example, if capture begins at area 612A, images are captured for each of the focal planes specified (e.g., five focal planes) before navigating to 612B. To achieve capture of images for each of the focal planes, the software directs commands to the microscope system to adjust the z-position of the microscope system (e.g., including adjustment based on the focal plane correction data), then the software captures the output of the camera. The image is compressed and saved for later retrieval. The areas (e.g., 612A and 612B) are typically defined so that there is some overlap for adjacent images.

The focal plane correction data can be interpreted in a variety of ways. In one example, the three near (e.g., the three nearest) points to the current location are considered. The proper z location value defines the z-axis. These three points define a plane, and the z value of a point on the plane at the current location is considered to be the proper z location.

In some cases, it may be advantageous to send the image to another computer. For example, an image capture computer may be particularly configured to handle the software and hardware requirements of controlling a microscope and interfacing with cameras. The image capture computer may send the captured images to another computer, which is particularly configured to store a large number of images and integrate them into composite images. Communication between the computers can be achieved in a variety of ways, such as standard networking protocols (e.g., the NETBEUI protocol, which is used by network systems of Microsoft Corporation). When the image is saved, it is accompanied by information indicating the location and focal plane from which it originated.

Overview of Integrating the Captured Images into Composite Images

After the images have been captured and stored, they are integrated into composite images. Typically, the images for a particular focal plane are integrated into a single composite image for the focal plane. Although the single composite image may comprise many image portions, it can be treated as a single image. For example, all image portions for the image can be preloaded into the computer's memory before browsing the image to avoid delay when a browsing user navigates within the composite image. Also, a single coordinate system can be used to specify a location within the composite image.

Figure 7:
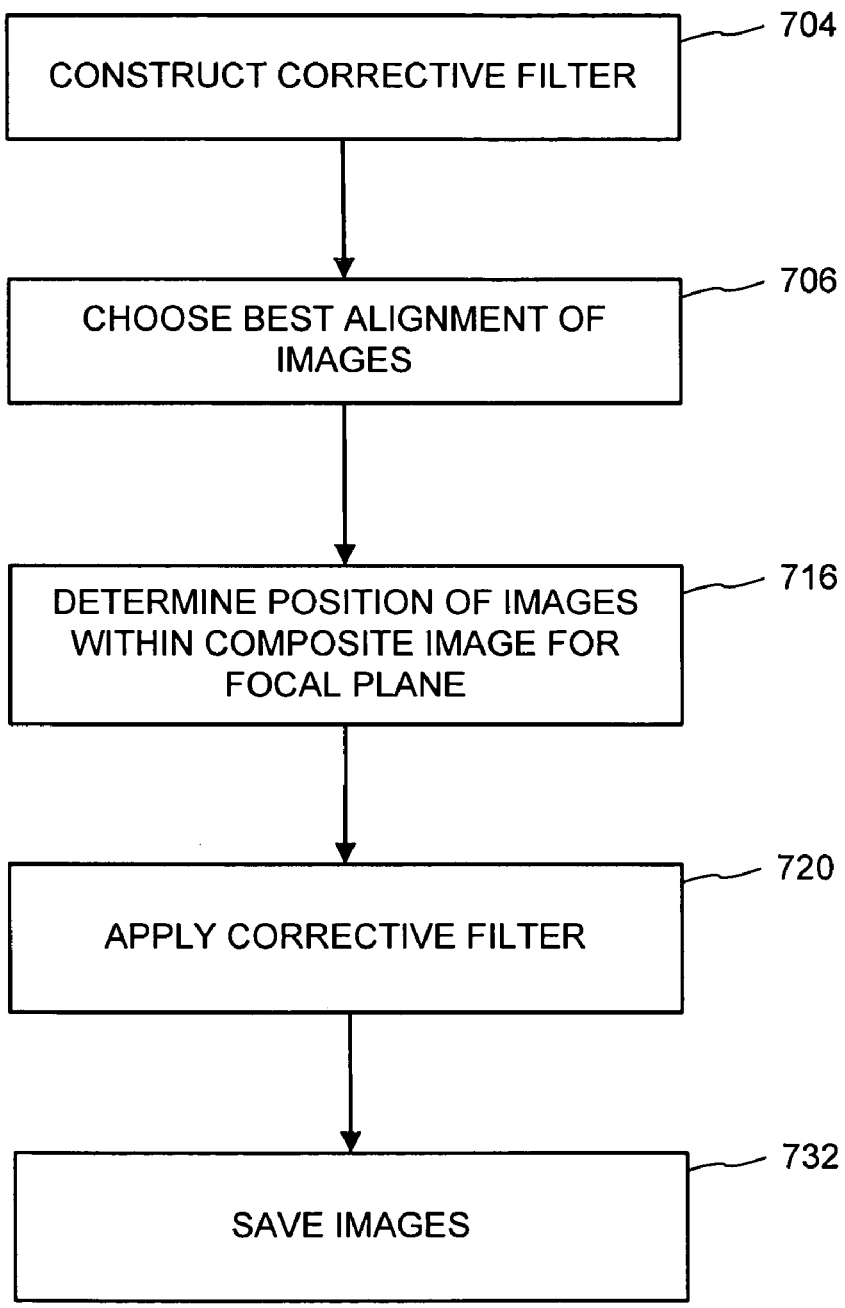
FIG. 7 is a flowchart showing a method for integrating captured images into composite images.

FIG. 7 is a flowchart showing an overview of a method for integrating images into composite images. The illustrated steps can be performed automatically by software. Typically, the images to be integrated are saved at a location (e.g., a directory or folder) on the hard disk of a computer, and a command is issued to the computer, which invokes the software to integrate the images into composite images.

At 704, a corrective filter is constructed for the images. The corrective filter avoids an effect called "tiling," and is described in more detail below. Typically, the corrective filter is constructed by analyzing color and brightness values for a set of images. The corrective filter can then be used for color correction functions.

At 706, a best alignment of images is chosen. Typically, a set of candidate alignments is generated for a particular image, and the best alignment is chosen based on comparison with adjacent images. Once the alignment is chosen, the position of the image within the composite image for a particular focal plane is determined at 716. During positioning, images may be cropped to eliminate extra, overlapping pixels.

At 720, the corrective filter is applied to the images (e.g., to achieve color correction), and at 732, the image portions of the composite images and any accompanying alignment data are saved. The image portions may comprise multiple captured images.

Details for Integrating the Captured Images into Composite Images

Figure 8:
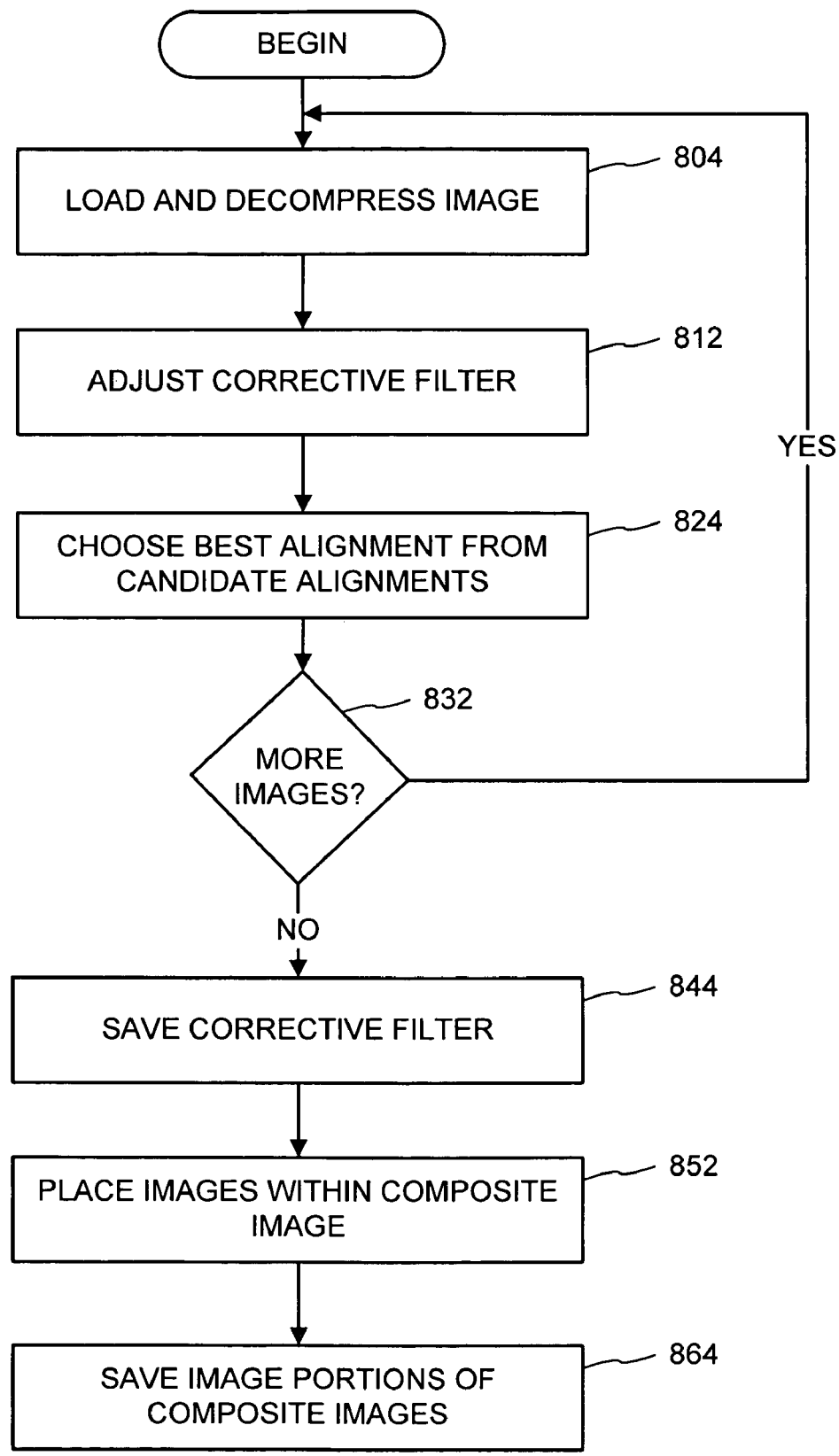
FIG. 8 is a flowchart showing a method for integrating captured images into composite images.

FIG. 8 shows a more detailed flowchart of a method for integrating captured images into composite images. In the example, the captured images are stored as compressed images (i.e., JPEGs) with accompanying information in a particular designated directory on a hard disk of a computer for integrating the images.

The method begins by choosing one out of the set of images to be integrated (e.g., first starting with the images of a particular focal plane). At 804, the image is loaded into memory from disk and decompressed.

Figure 9:
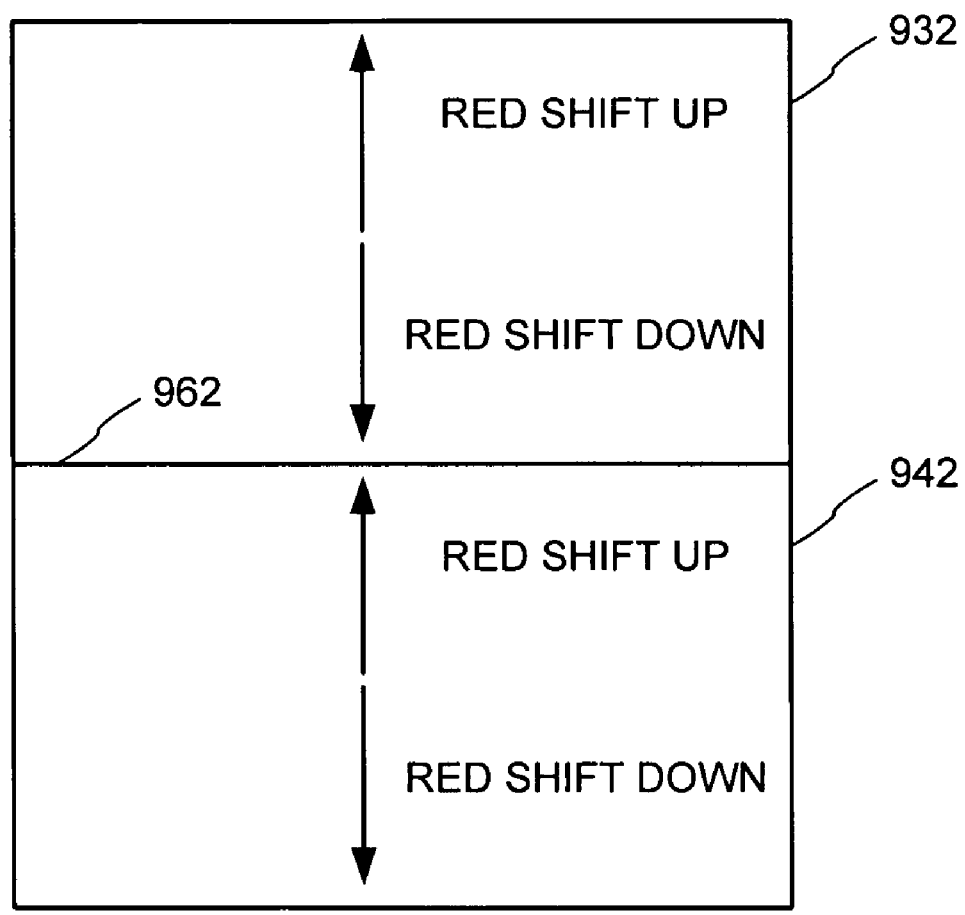
FIG. 9 is a block diagram illustrating a phenomenon called "tiling" that can occur when two images are joined.

At 812, the image is used to adjust the corrective filter. The corrective filter can be employed to avoid an effect called "tiling." Due to the optical characteristics of a microscope system, captured images often exhibit a shift in color, brightness, or both. For example, a captured image may represent an area of a slide that has a uniform background. Even though the area has a uniform background, the top of the slide may appear redder than the bottom of the slide. Such an effect is illustrated in FIG. 9. When a first captured image 932 exhibiting the color shift is adjoined to a second captured image 942 exhibiting the same color shift, the edge 962 becomes apparent.

It is thus obvious to the observer that the composite image presented has been constructed from two images (i.e., "tiles"). By revealing that the composite image has been artificially constructed by a computer, the tiling effect can cause the observer to refuse to accept that the image is accurate and authentic. Further, even if the observer accepts the image, the tiling effect can become so pronounced that it distracts the observer from recognizing features in the composite image. Thus, it is desirable to avoid the tiling effect when presenting composite images. Tiling can be avoided via construction of a corrective filter.

Figure 10:
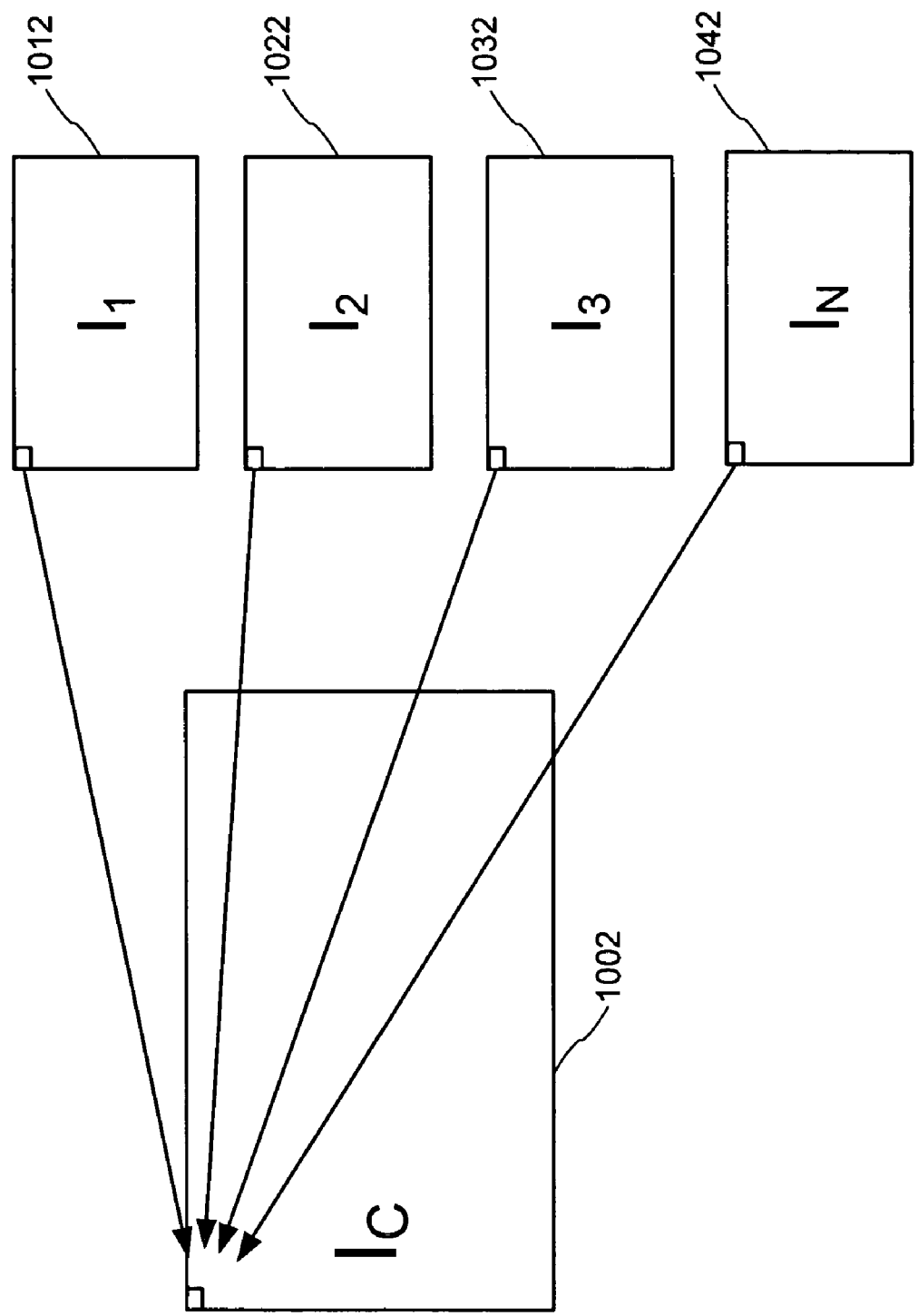
FIG. 10 is a block diagram illustrating construction of a corrective filter for avoiding tiling.

FIG. 10 illustrates construction of a corrective filter for avoiding tiling. For a set of captured images (e.g., all captured images), a corrective filter is constructed by considering the pixels in the set of captured images at the same location. The corrective filter thus takes the form of a two dimensional array of red, green, and blue correction values representing an average for captured images in the set.

For example, in FIG. 10, a pixel in the upper left corner of the corrective filter image ($I_c$) 1002 is generated by considering the pixels in the same location (i.e., the upper left corner) of the captured images in the set ($I_1$-$I_n$) 1012-1042. The same approach is used for other pixels in the images. A typical implementation simply adds the color and brightness values to an accumulated total after each image is decompressed. The corrective filter image is then computed by finding separate averages for color and brightness values (e.g., by dividing by the total number of images). Other approaches can be used (e.g., by dividing as the values are accumulated). The bitmap representing the corrective filter image is then saved.

Generally, the corrective filter image will represent optical characteristics of the microscope system, including color shift. In the event there are smudges or other imperfections in the microscope's optics, these will also be represented by the corrective filter. Subsequently, the corrective filter can be applied to the images to avoid tiling and cancel out imperfections in the microscope system.

Returning now to FIG. 8, at 824, the best alignment from candidate alignments is chosen by the software. Typically, for a particular captured image, an alignment for the horizontally adjacent captured image is chosen, then an alignment for the vertically adjacent captured image is chosen. The software then considers the next captured image (e.g., one that has just been aligned).

Figure 11:
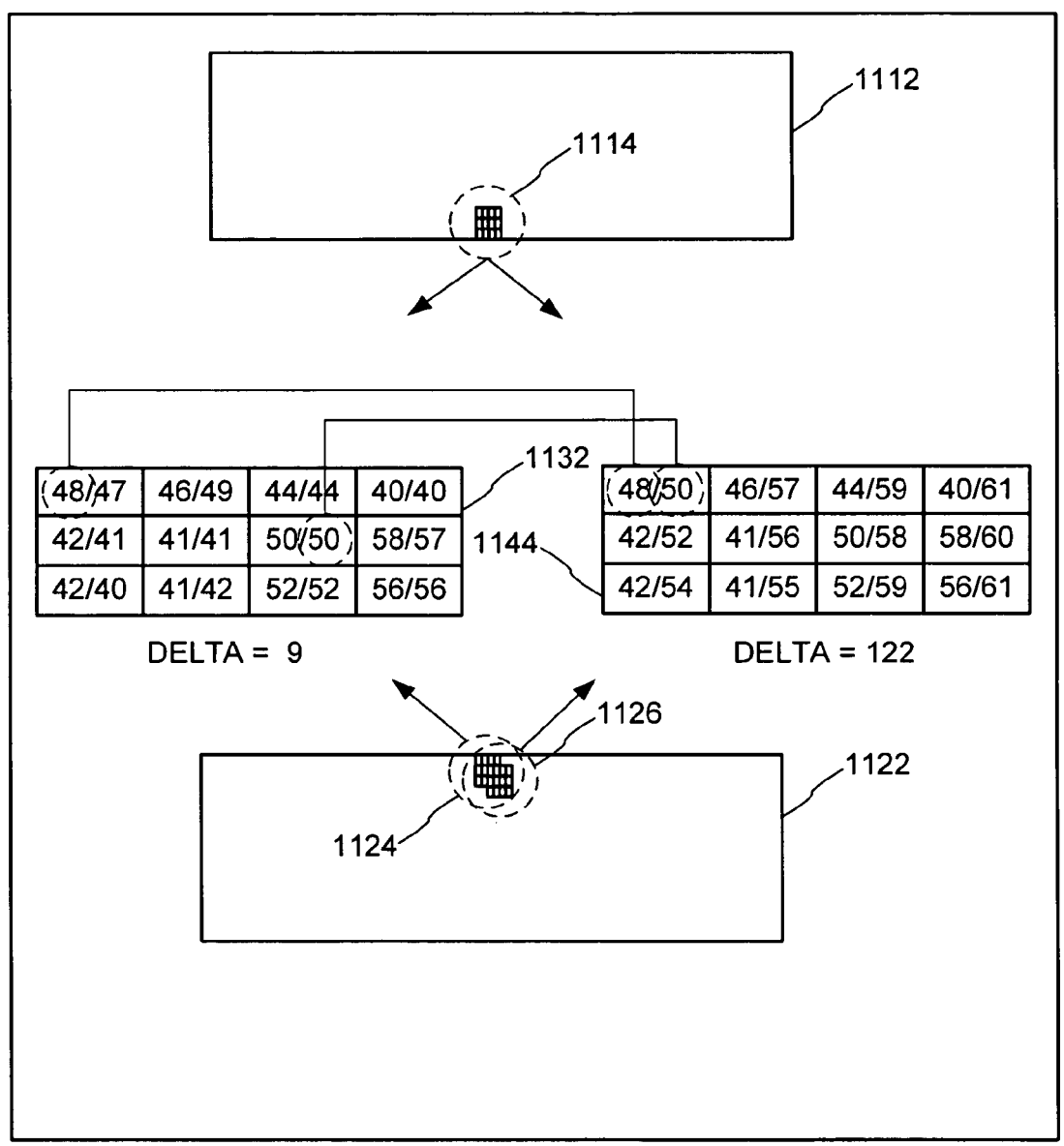
FIG. 11 shows an example of choosing an alignment for two vertically adjacent captured images.

An example of choosing an alignment between two captured images is shown in FIG. 11. Typically, a number of candidate alignments are considered, and each is given a score. Alignments are designated by an offset. For example, consider an alignment in which two captured images match perfectly from end; such an alignment corresponds to an (X,Y) offset of (0,0). As one captured image is moved relative to another, the offset changes. Since there is typically some overlap between adjacent captured images, the offset is usually not (0,0).

The score for an alignment can be calculated by comparing color and brightness values for two images that are to be aligned. In the example shown in FIG. 11, two captured images 1112 and 1122 are being aligned. For purposes of illustration, only a small portion of the captured images are shown. Two candidate alignments are shown in the example; the area 1114 of the captured image 1112 is compared, pixel by pixel, to the area 1124 of the captured image 1122 in the first candidate alignment. The area 1114 of the captured image 1112 is compared to the area 1126 of the captured image 1122 in the second candidate alignment. Two corresponding comparisons 1132 and 1144 are shown. In the example, brightness levels for each pixel are compared. The first number in each box indicates a brightness level for the first captured image 1112, and the second number indicates a brightness level for the second captured image 1122.

For the first candidate alignment 1132, a score of 9 is assigned, based on the differences (e.g., sum of absolute values of differences) of the brightness levels of the pixels considered. For the second candidate alignment 1144, a score of 122 is assigned, based on the differences of the brightness levels. Since the first candidate alignment has a better score (i.e., fewer differences), it is chosen as the better of the two alignments.

In practice, many more candidate alignments and many more pixels are considered, and color as well as brightness levels can be considered. In some scenarios, a pixel sample suffices, rather than a pixel by pixel approach. The parameters for the comparison can be adjusted depending on various scenarios (e.g., characteristics of the biological material being observed or the microscope system). As a result of choosing an alignment, a horizontal and vertical offset value is specified indicating how the two captured images can be positioned to properly align them. The offset values are saved (e.g., in an array), and then it is determined whether there are more images at 832. If so, another captured image is loaded and decompressed at 804. Otherwise, the corrective filter is saved at 844.

In the example, a composite image is represented as a set of uniformly sized, compressed images (e.g., JPEGs) called composite image portions. At 852, after the four corners of the composite image have been established, the composite image portions of the composite images are saved. Typically, saving the composite image portions includes cropping the captured images to remove overlap between adjacent images, if any.

Figure 12:
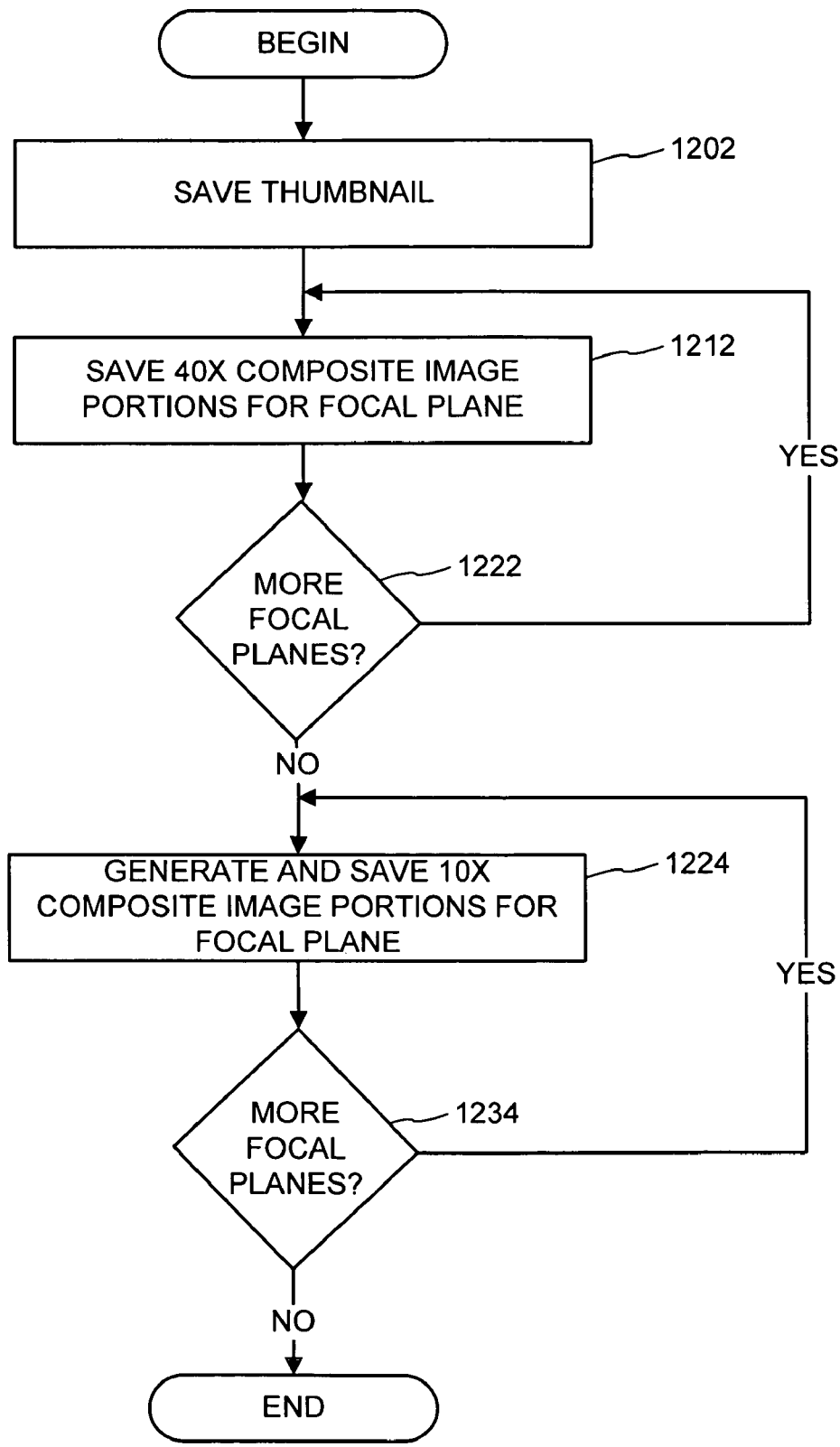
FIG. 12 shows a method for saving composite image portions for composite images.

A method for saving the image portions of the composite images is shown in more detail in FIG. 12. At 1202, a thumbnail (e.g., overview of the entire captured area) is saved to a file. Then, at 1212, the 40× composite image portions for a particular focal plane are saved. At 1222, if there are more focal planes, execution continues at 1212. Then, at 1224, 10× composite image portions for a particular focal plane are saved. The 10× composite image portions are generated by condensing the 40× image, such as by considering a 4×4 square of pixels from a 40× image for each pixel in the 10× composite image. In this way, images for two different magnifications are generated from images captured at a single magnification. Alternatively, the 10× image could be generated from the captured images and integrated separately. At 1234, if there are more focal planes, execution continues at 1224.

Figure 13:
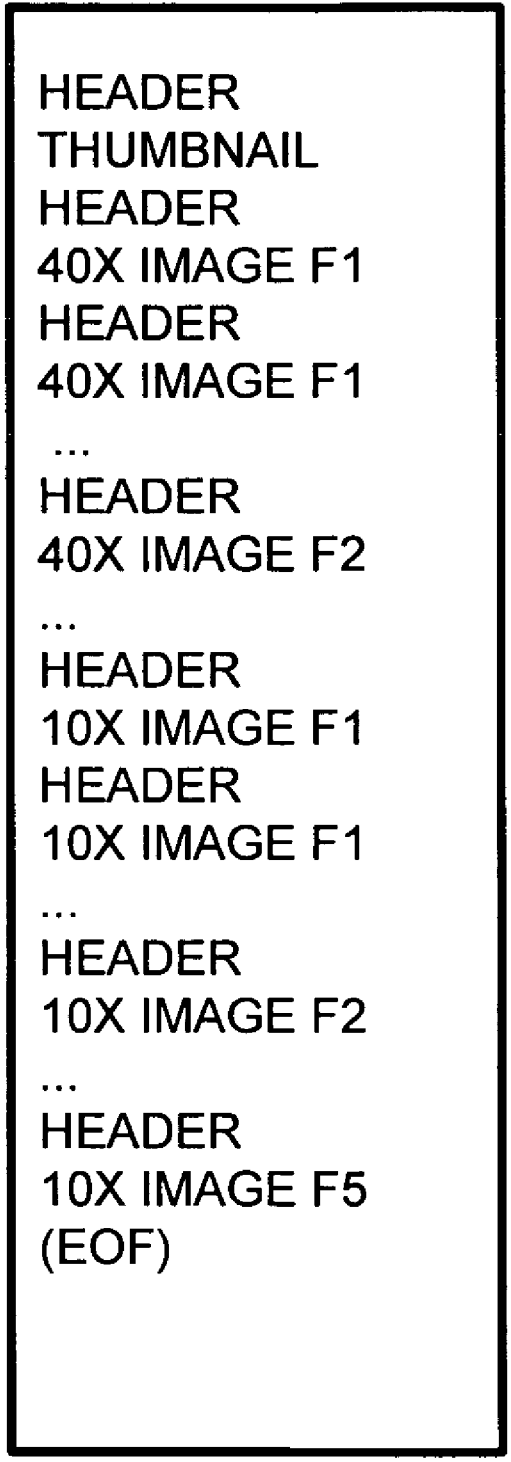
FIG. 13 shows a file format for saving composite image portions for various focal planes.

As a result of these manipulations, the information can be stored in a single file in a format 1304 as shown in FIG. 13.

Saving the composite image portions in a single file has the advantage of requiring far fewer file open operations when the file is saved (as compared to a scenario in which each composite image portion is saved in a separate file). Subsequently, when the images are retrieved, far fewer file open operations are required as compared to an arrangement in which each composite image portion is saved in a separate file. In some cases, the order of the composite image portions within the file does not matter because the classification (e.g., location and focal plane) of the composite image portions can be determined by their headers.

Figure 14:
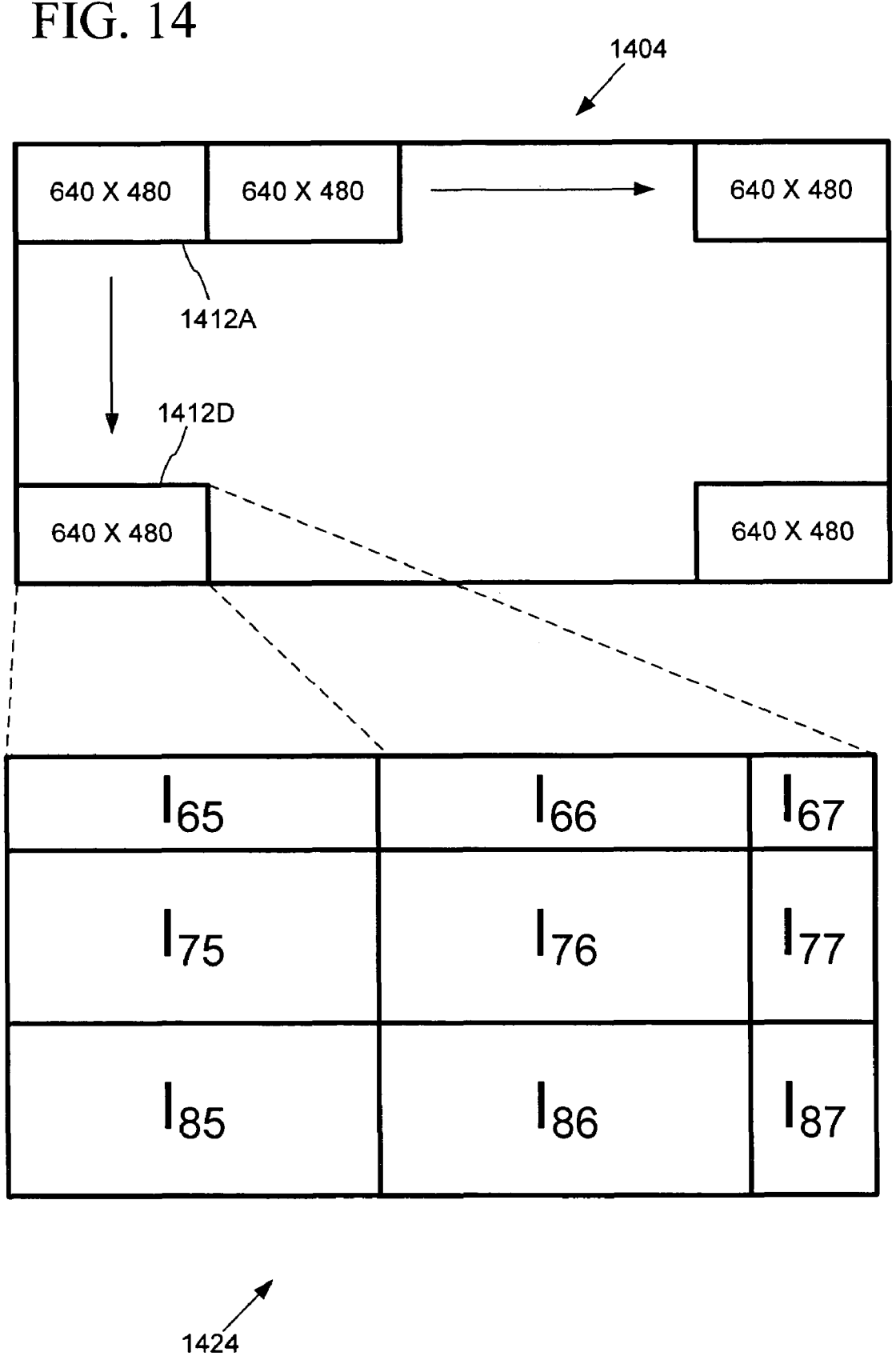
FIG. 14 shows an example of generating composite image portions of uniform size from captured images.

Generation of the composite image portions can be conducted in such a manner so that they are of uniform size (e.g., 640 by 480 pixels) as shown in FIG. 14. For the composite image 1404 generated for a particular focal plane, a number of uniformly-sized composite image portions (e.g., 1412A) can be generated by assembling a number of smaller captured images (or portions thereof) into a single composite image portion. In the example, the composite image portion 1412D is generated by combining captured images (I65, I66, I67, I75, etc.) as shown in the exploded view 1424. The alignment of the adjacent images is determined by the offsets determined as described above. As the composite image portions are generated, overlap between adjacent images can be discarded.

As a result of the technique shown in FIG. 14, the composite images for plural focal planes can be saved in a single file, and the composite image portions are saved as images (e.g., JPEGs) of uniform size.

Browsing the Composite Images

After the captured images have been integrated into composite images and stored on a computer-readable medium, the composite images can be browsed by any computer having proper browsing software. Transferring the composite images to a browsing computer can be achieved in any number of ways. The composite images can be shipped on physical media (e.g., CD-ROM or magnetic floppy disk) or downloaded over a network (e.g., the Internet).

The browsing computer has software that enables a computer user to browse the composite images to simulate viewing the biological material under a microscope. The composite image is typically viewed on a video display and navigated via a keyboard or pointing device. For example, in a file having composite images for five focal planes at two different magnifications, the computer user can navigate to various locations within the composite images. If the user finds an area of interest at low magnification, the user can switch to high magnification to zero in on an area of interest. Since plural focal planes are represented, the computer user can also navigate to various depths of the specimen (e.g., navigate along a z-axis).

Because the area captured is sufficiently represented by the composite images, the composite images can be used for a variety of purposes. For example, the images can be used for Pap tests, for training cytotechnicians and pathologists how to evaluate Pap tests, and for demonstrating that a cytotechnician or pathologist has sufficient skill to accurately analyze Pap tests.

Figure 15:
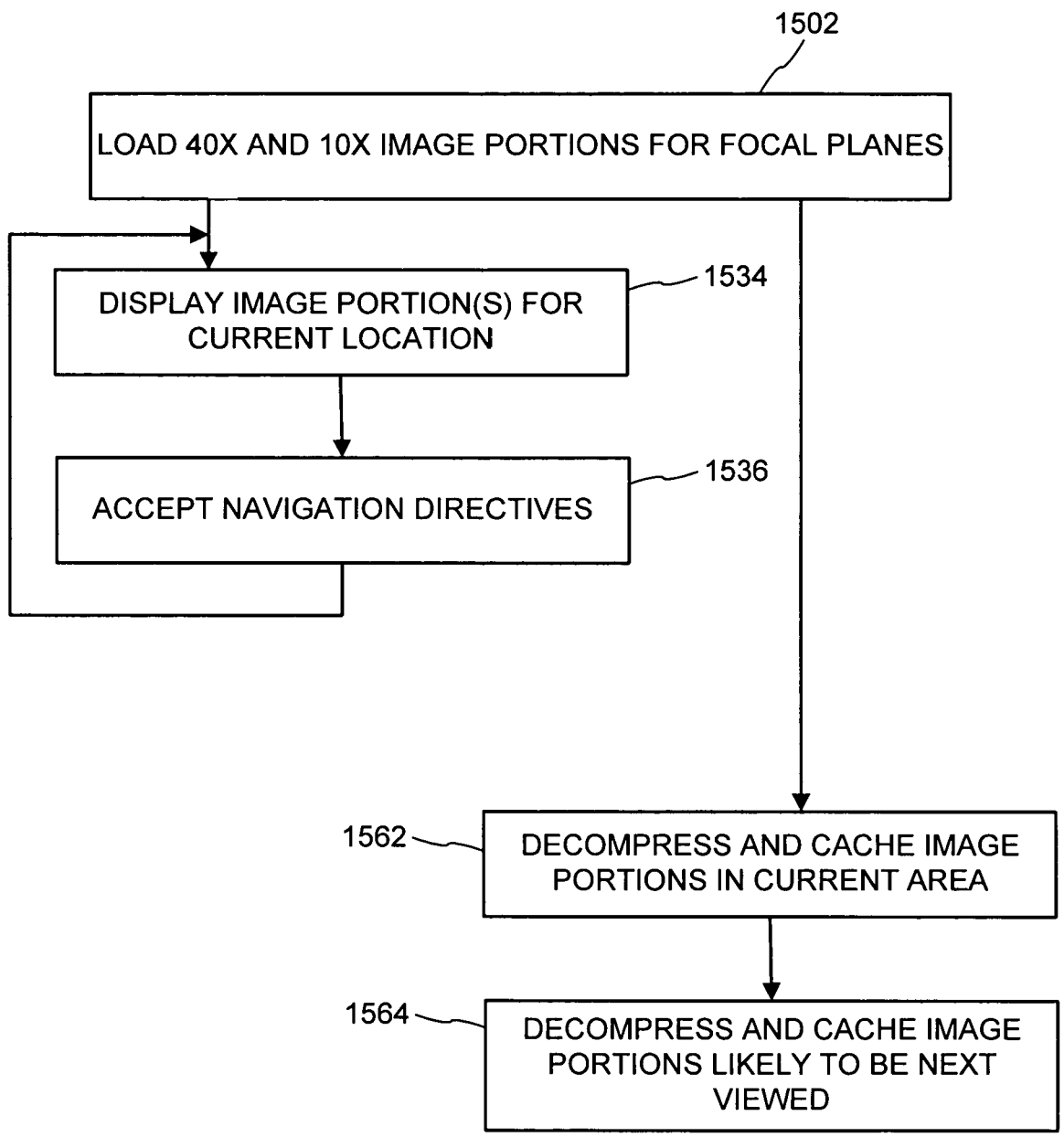
FIG. 15 shows an example of a computer-implemented method for browsing composite images.

An example of a computer-implemented method for browsing composite images is shown in FIG. 15. In the example, the method is implemented in the DELPHI programming language available from Inprise Corporation (Borland) of Scotts Valley, Calif. on an INTEL-based computer system. However, the method can be implemented on any of a variety of computer systems in a variety of languages. In the example, the computer system has sufficient memory to hold all of the composite images in a compressed form and runs two threads simultaneously. While one thread handles the task of navigating throughout the images, the other thread decompresses some of the images in advance to avoid delay when the computer user navigates throughout the images. Although a multi-threaded implementation is shown, logic can be constructed to achieve similar results without multi-threading. Alternatively, multi-tasking can be used.

At 1502, entire composite images for 40× and 10× magnifications are loaded into memory for each of the focal planes in compressed form (e.g., a set of 640 by 480 JPEGs). In the example, all the composite image portions and appropriate headers are stored in a single (e.g., 250 Mb) file. Such an approach requires only a single open command to the file system and greatly reduces the overhead required to deal with the composite image portions. The composite image portions in the file need not be in any particular order. A data structure (e.g., array) tracks the location of each of the compressed composite image portions in memory. By loading an entire composite image into memory, delay during navigation of the image is avoided.

Figure 16:
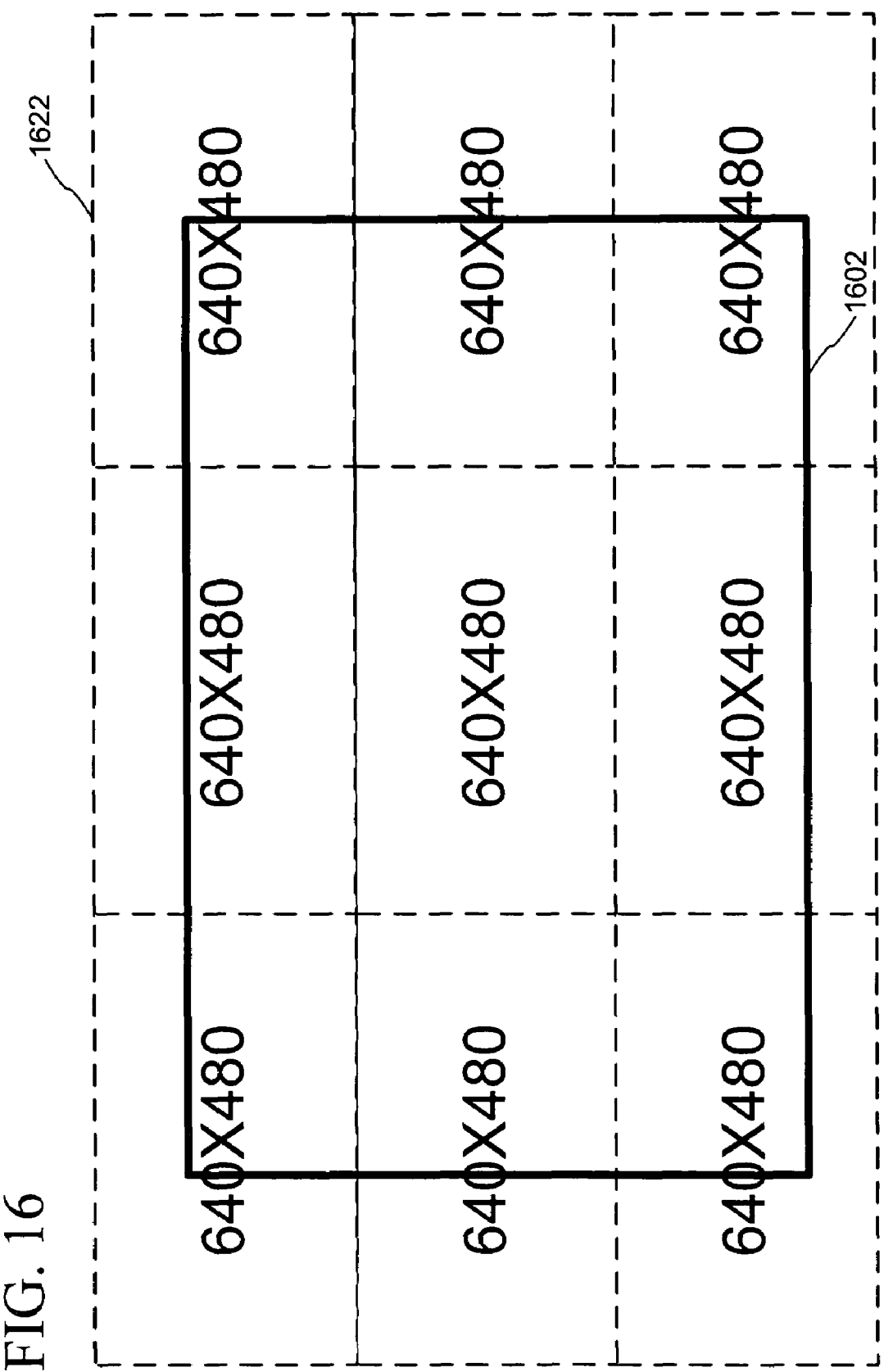
FIG. 16 shows a block diagram of composite image portions and a current browsing area.

During operation, the software tracks a current browsing area within the composite image (e.g., an X, Y, and Z location). FIG. 16 shows a browsing scenario in which the current browsing area 1602 is being viewed. Internally, the current area 1602 may be tracked in a number of ways (e.g., by tracking an X, Y, and Z location of the upper left hand corner). Typically, the size of the current area 1602 remains constant, although it can be resized if the display window is resized.

At 1534, a first thread displays composite image portions for the current location in the current browsing area 1602. To display the current browsing area 1602 on the video display of the browsing computer system, the browsing software displays the composite image portions (e.g., portion 1622) that fall within the current browsing area 1602. Some portions of the composite image portions (e.g., the upper right portion of the portion 1622) are not visible, but come into view when the browsing user navigates (e.g., to the upper right of the composite image). In the example, there are typically nine composite image portions being viewed, although in rare circumstances there may be only four.

At 1536, the software accepts navigation directives from a browsing user. For example, the user may use a keyboard (e.g., arrow keys) or a pointing device (e.g., a mouse) to navigate the image and choose a different focal plane or magnification. If a composite image portion is temporarily unavailable (e.g., not yet decompressed), a grey rectangle is displayed until the image portion is available.

At 1562, a second thread decompresses and caches the composite image portions in the current area for the current focal plane. The current area takes a high priority. At 1564, after the current area is decompressed and cached, the first thread begins decompressing and caching composite image portions that are outside the current browsing area but likely to be next viewed for the same magnification. In the example, composite image portions adjacent to the current area in x and y directions are decompressed with high priority, but less priority than the current area. Then, composite image portions adjacent to the current area in the z direction are decompressed and cached with a lower priority.

As the images are displayed, another level of caching takes place. A video memory cache manager caches the images in video memory. The video memory is then mapped to an appropriate location on the screen. Typically, computer video interfaces provide extremely efficient functions for achieving such mapping. Up to fifteen images are stored in the video memory cache. The software employs MICROSOFT DIRECTX technology developed by Microsoft Corporation of Redmond, Wash., to map video memory to the screen and more directly access video memory without the additional overhead typically associated with a window manager. In this way, when the computer user navigates to an area requiring view of an adjacent composite image portion, the composite image portion may already be decompressed and loaded into video memory and can be quickly mapped to a location on the screen. Thus, the browsing method shown avoids delaying availability of image portions to the browsing computer user.

Figure 17:
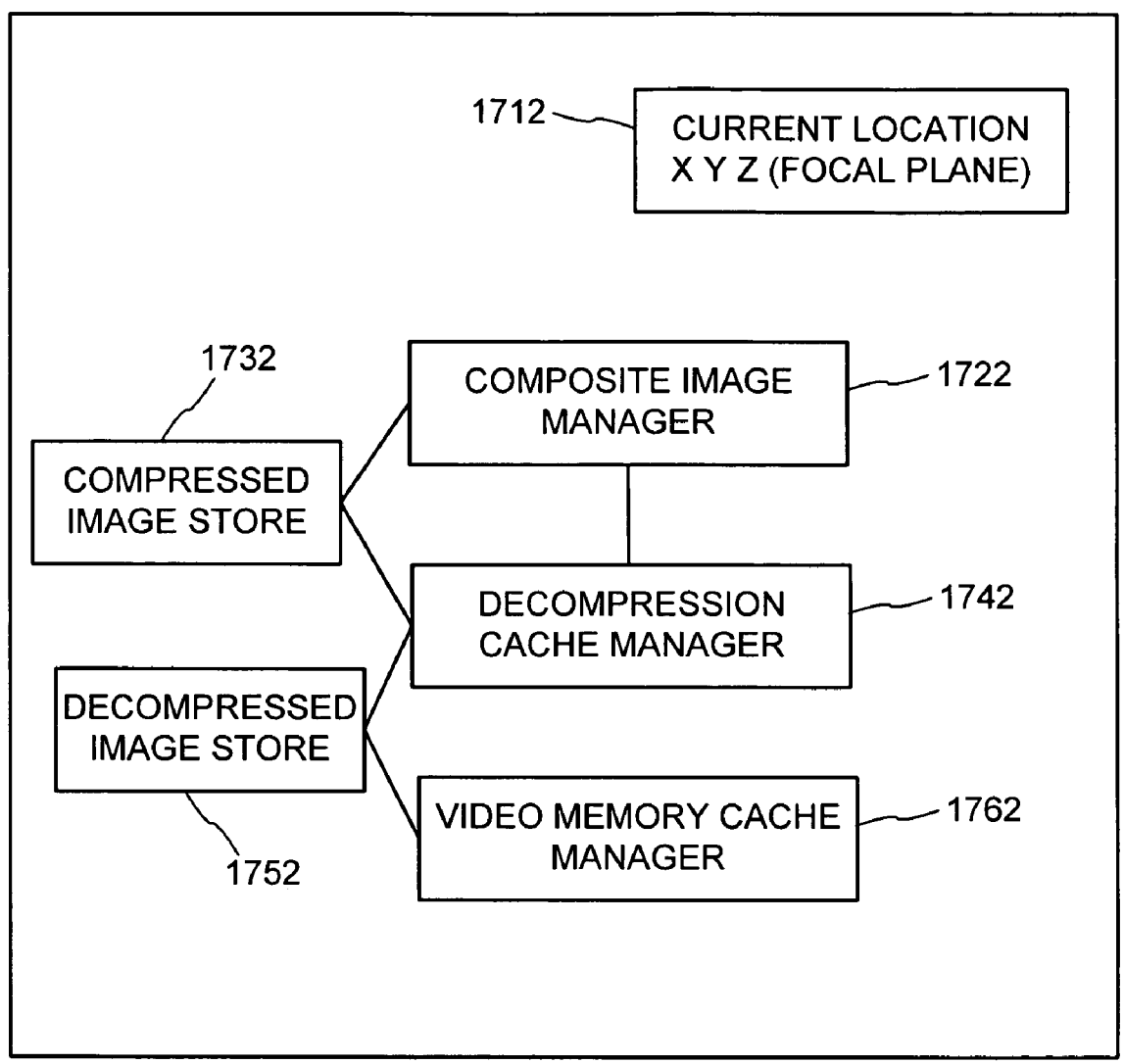
FIG. 17 shows a block diagram of a caching system for maintaining decompressed composite image portions.

An exemplary caching system is shown in FIG. 17. The current area being browsed is stored in memory in current location variables 1712. The composite images for each of the focal planes are stored in memory as compressed images and accessible via a composite image manager 1722. The composite image manager 1722 tracks the location in memory of each of the composite image portions, which are stored in the compressed image store 1732. Typically, the compressed image store 1732 contains entire composite images in compressed form (e.g., a set of JPEGs that make up an entire composite image).

The decompression cache manager runs on a thread separate from the navigation logic. Appropriate images according to a specified priority are fetched by consulting the composite image manager 1722, decompressed, and placed in a decompressed image store 1752 in memory. In this way, the images are pre-decompressed (i.e., decompressed before they are needed for display). As images are required for display, they are moved into video memory and tracked by the video memory cache manager 1762.

In the example, the video memory cache manager 1762 allows up to fifteen images (e.g., composite image portions) to reside in video memory at a time. The least recently used images are discarded when a new image needs to be loaded into video memory due to browsing user navigation.

Example Implementation

In an example implementation, images for five focal planes were captured at 40× magnification. There were a total of 18,550 captured images (3,710 per focal plane), each of dimensions 640 by 480 and being about 100 Kb in size. The captured images were saved as separate files according to a file naming convention enabling them to be reloaded for integration. The first letter of the file indicated the focal plane (e.g., A, B, C, D, or E), the next two digits indicated a logical x position, and the next two digits indicated a logical y position.

After being stitched together, recompressed, and color corrected, five composite images were generated having a total of 9,976 image portions (including one color-correction image) of dimensions 640 by 480, taking up a total of 636 Mb. These images were saved in a single file, including header information indicating the focal plane and position of each image. 10× composite images (having 108 image portions per composite image) were generated from the integrated 40× images, and a thumbnail of dimensions 960 by 540 was also generated for the center focal plane. The thumbnail, 40× composites for five focal planes, and 10× composites for the five focal planes were saved in the same file.

During integration, alignment of adjacent images in the x,y dimensions was achieved by calculating scores for a default of five regions. Each region was 128 by 128 pixels, and each combination of overlap was considered (e.g., 1 over, 2 over, 3 over, . . . , 1 up and 1 over, 1 up and 2 over, . . . 128 up and 1 over, etc.). Rather than using manual iterative calculations, an algorithm applied Fourier transform techniques.

ALTERNATIVES

Although the above examples show capturing images as 40× magnification, a different magnification can be used. Similarly, although a 10× magnification is generated from the 40× images, a different magnification can be generated. Further, although the described technology can be particularly useful for assisting in certifying the competence of cytotechnicians and pathologists, the technology can be used for a variety of other scenarios relating to simulating viewing an item under a microscope. In view of the many possible embodiments to which the principles of the invention may be applied, it should be recognized that the illustrated embodiments are examples of the invention, and should not be taken as a limitation on the scope of the invention. Rather, the scope of the invention is defined by the following claims. We therefore claim as our invention all that comes within the scope and spirit of these claims.

We claim:

1. A computer-implemented method of browsing a composite image representing an item viewed under a microscope, wherein the composite image comprises a set of composite image portions, the method comprising:

decompressing the composite image portions of the composite image for a browsing area currently being browsed at a computer;

displaying at least portions of the decompressed images; and decompressing composite image portions of the composite image that are outside the browsing area currently being browsed and likely to be next displayed during navigation of the composite image.

2. The method of claim 1 wherein the item is a biological sample.

3. The method of claim 1 further comprising:

loading into memory at least one complete composite image for a focal plane in compressed form.

4. The method of claim 1 further comprising:

loading into memory complete composite images for plural focal planes in compressed form.

5. The method of claim 1 wherein the composite image portions likely to be next displayed are composite image portions adjacent to and in a same focal plane as composite image portions currently being displayed.

6. The method of claim 1 wherein the composite image portions likely to be next displayed are composite image portions adjacent to composite image portions currently being displayed and in a different focal plane.

7. The method of claim 1 wherein displaying is performed by a first thread; and decompressing images likely to be next displayed is performed by a second thread.

8. The method of claim 1 further comprising:

in preparation for displaying at least portions of the decompressed images, loading the decompressed images directly into video memory;

tracking which images are loaded into video memory;
tracking when images loaded into video memory were last used; and
keeping images in video memory until display of an image requires discarding an image, wherein the least recently used image is discarded.

9. A computer-readable medium comprising computer-executable instructions for performing the method of claim 1.

10. A browsing system for displaying composite images comprising a set of compressed images forming portions of the composite images, the system comprising:
 variables for tracking the current browsing area;
 a composite image manager for providing access to the portions of the composite images;
 a decompression cache manager for tracking pre-decompressed images;
 a decompressed image store for storing decompressed versions of the portions of the composite images;
 a video memory cache manager for tracking which of the decompressed versions of the portions of the composite images are currently loaded in video memory.

11. The browsing system of claim 10 wherein the composite image manager maintains a store of composite images for a plurality of focal planes.

12. The browsing system of claim 10 wherein the composite image manager maintains in memory a store of at least one complete composite image in compressed form.

13. The browsing system of claim 10 wherein the composite image manager maintains in memory a store of a plurality of complete composite images for a plurality of focal planes in compressed form.

14. The browsing system of claim 10 wherein the decompression cache manager prioritizes decompression according to the following, ordered priority:
 image portions for the current browsing area;
 image portions in a same focal plane and adjacent to the current browsing area; and
 image portions in a different focal plane and adjacent to the current browsing area.

15. A browsing system for displaying composite images comprising a set of compressed images forming portions of the composite images, the system comprising:
 means for tracking the current browsing area;
 means for providing access to the portions of the composite images;
 means for tracking pre-decompressed images;
 means for storing decompressed versions of the portions of the composite images;
 means for tracking which of the decompressed versions of the portions of the composite images are currently loaded in video memory.

* * * * *